United States Patent
Hou et al.

(10) Patent No.: US 12,163,410 B2
(45) Date of Patent: Dec. 10, 2024

(54) METHOD AND APPARATUS FOR PREDICTING OPTIMAL EXPLOITATION IN SHALE OIL IN-SITU CONVERSION

(71) Applicant: PetroChina Company Limited, Beijing (CN)

(72) Inventors: Lianhua Hou, Beijing (CN); Jinghong Wang, Beijing (CN); Jingwei Cui, Beijing (CN); Zhongying Zhao, Beijing (CN)

(73) Assignee: PETROCHINA COMPANY LIMITED, Beijing (CN)

( * ) Notice: Subject to any disclaimer, the term of this patent is extended or adjusted under 35 U.S.C. 154(b) by 463 days.

(21) Appl. No.: 17/269,906

(22) PCT Filed: Feb. 24, 2020

(86) PCT No.: PCT/CN2020/076344
§ 371 (c)(1),
(2) Date: Oct. 15, 2021

(87) PCT Pub. No.: WO2021/017460
PCT Pub. Date: Feb. 4, 2021

(65) Prior Publication Data
US 2022/0034213 A1 Feb. 3, 2022

(30) Foreign Application Priority Data
Jul. 26, 2019 (CN) .............................. 201910680547

(51) Int. Cl.
*G06F 11/30* (2006.01)
*E21B 43/24* (2006.01)
(Continued)

(52) U.S. Cl.
CPC .............. *E21B 43/30* (2013.01); *E21B 43/24* (2013.01); *G01N 25/18* (2013.01); *G01N 33/241* (2013.01);
(Continued)

(58) Field of Classification Search
CPC ...................................................... E21B 43/30
See application file for complete search history.

(56) References Cited

U.S. PATENT DOCUMENTS

2007/0246994 A1* 10/2007 Kaminsky ............. E21B 43/241
166/244.1
2011/0132600 A1 6/2011 Kaminsky et al.
(Continued)

FOREIGN PATENT DOCUMENTS

CN 106951686 A 7/2017
CN 107688669 A 2/2018
(Continued)

OTHER PUBLICATIONS

Y. Fan et al, Numerical Simulation of the In-Situ Upgrading of Oil Shale, 2010 SPE Journal, pp. 1-14 (Year: 2010).*
(Continued)

*Primary Examiner* — Phuong Huynh
(74) *Attorney, Agent, or Firm* — The Dobrusin Law Firm, P.C.; Daniela M. Thompson-Walters

(57) ABSTRACT

The disclosure provides a method and apparatus for predicting an optimal exploitation approach for shale oil in-situ conversion. The method includes: determining a lower limit temperature required for completely converting convertible organic matter in a shale to be measured into oil and gas, based on a pre-established relationship between the temperature rise rate and the lower limit temperature; determining an optimal well distance of heating wells, based on a thermal field parameter of a target reservoir of interest, an
(Continued)

optimal heating time corresponding to the lower limit temperature, and a pre-established relationship between an optimal well distance of heating wells and the optimal heating time; determining an oil yield equivalent based on a temperature and an oil yield equivalent of the shale; determining an optimal well pattern; the lower limit temperature, the optimal well distance of heating wells, the oil yield equivalent and the optimal well pattern are optimal parameters.

20 Claims, 11 Drawing Sheets

(51) Int. Cl.
  *E21B 43/30* (2006.01)
  *G01N 25/18* (2006.01)
  *G01N 33/24* (2006.01)
  *G06Q 10/04* (2023.01)
  *G06Q 50/02* (2012.01)
(52) U.S. Cl.
  CPC ............. *G06Q 10/04* (2013.01); *G06Q 50/02* (2013.01); *E21B 2200/20* (2020.05)

(56) References Cited

U.S. PATENT DOCUMENTS

| | | | |
|---|---|---|---|
| 2016/0115771 A1 | 4/2016 | Ganguly et al. | |
| 2020/0018145 A1* | 1/2020 | Hou | E21B 49/00 |
| 2020/0018740 A1* | 1/2020 | Hou | G06Q 10/04 |
| 2022/0034213 A1 | 2/2022 | Hou et al. | |

FOREIGN PATENT DOCUMENTS

| | | | |
|---|---|---|---|
| CN | 107818188 A | | 3/2018 |
| CN | 107818518 A | | 3/2018 |
| CN | 108547612 A | | 9/2018 |
| CN | 109113699 A | | 1/2019 |
| CN | 109113730 | * | 1/2019 |
| CN | 109657299 A | | 4/2019 |
| CN | 109113730 A | | 1/2020 |
| EP | 3812983 A1 | | 4/2021 |
| RU | 2663526 C1 | | 8/2018 |
| RU | 2692369 C1 | | 6/2019 |
| WO | 2021017460 A1 | | 2/2021 |

OTHER PUBLICATIONS

International Search Report, Application No. PCT/CN2020/076344, dated May 22, 2020.
Chinese Search Report. Application No. 201910680547.3, dated Jul. 22, 2019.
Compilation of abstracts of the 2015 annual meeting of the Chinese Geological Society, Influence and Enlightenment of Different Boundary Conditions on In-situ Conversion and Production of Oil Shale.
China Mining Magazine, vol. 20 No. 6, New development of oil shale in-situ technology dated Jun. 2011.
Russian Office Action and Search Reported dated Nov. 8, 2021, Application No. 2021102059.
First Office Action and Search Report issued on Feb. 11, 2022 for counterpart Canadian patent application No. 3,109,204.
Extended European Search Report issued on Mar. 25, 2022, EP Patent Application No. 20837921.4.
Y.Fan et al., Numerical Simulation of the In-Situ Upgrading of Oil Shale; 2010 SPE Journal, pp. 1-14.
EP Office Action dated Feb. 8, 2024, Application No. 20 837 921.4.

* cited by examiner

METHOD AND APPARATUS FOR PREDICTING OPTIMAL EXPLOITATION IN SHALE OIL IN-SITU CONVERSION

CROSS-REFERENCE TO RELATED APPLICATIONS

This application claims priority to Chinese Patent Application No. 201910680547.3, entitled "METHOD AND APPARATUS FOR PREDICTING AN OPTIMAL EXPLOITATION APPROACH FOR SHALE OIL IN-SITU CONVERSION", filed on Jul. 26, 2019, both of which are hereby incorporated by reference in their entireties.

TECHNICAL FIELD

This disclosure relates to the technical field of shale oil and gas exploration and exploitation, and in particular to a method and apparatus for predicting an optimal exploitation approach for shale oil in-situ conversion.

BACKGROUND

Shale oil contains retained oil and unconverted organic matter in shale. According to the difference in the maturity of organic matter (vitrinite reflectance Ro), the shale oil is divided into the shale oil with medium to high maturity (Ro≥0.95%) and the shale oil with medium to low maturity (Ro<0.95%).

The shale oil with medium to high maturity has become an important area of oil exploration and exploitation in the world. In the practice of the exploration and exploitation it has proved that it is impossible to achieve exploitation with the existing horizontal well volume fracturing technique, as the maturity of organic matter of the shale with the low to medium maturity is not high, the porosity in shale is not well-developed, and flow of fluid is made difficult. However, the shale with the low to medium maturity can be exploited by using an in-situ conversion technique.

It is roughly estimated that globally, recoverable oil resource that can be exploited from the organic matter-rich shale with the low to medium maturity by using the in-situ conversion technique amounts to about 1.4 trillion tons, and recoverable gas resource amounts to about 1,100 trillion cubic meters. While in China, recoverable oil resource that can be exploited from shale by using the in-situ conversion technique amounts to about 70-90 billion tons, and recoverable gas resource amounts to about 57-65 trillion cubic meters. These figures are more than 3 times of the recoverable resource that can be exploited by using conventional oil and natural gas technologies, which is very promising. With the current production scale of 7.5 billion tons/year of the crude oil output in the world, the resource of shale oil with the medium to low maturity can be developed for about 200 years by using the in-situ conversion technology, which thus has a bright future.

However, the shale oil in-situ conversion exploitation technology is different from the existing horizontal well volume fracturing technology. The in-situ conversion exploitation is a technology in which an effective shale section is heated by utilizing a horizontal well or a vertical well, so as to convert the retained oil and gas as well as the unconverted organic matter in a layer of effective shale into lightweight oil and natural gas and to realize the exploitation. The existing shale oil in-situ conversion exploitation schemes, which are mainly used for the in-situ exploitation of shallow oil shale and focus on the study of in-situ exploitation method technology itself, have problems that the exploitation approach of shale oil in-situ conversion is unreasonable and the cost of exploitation is high, thus it is impossible to effectively guide shale oil in-situ conversion exploitation.

Regarding the above technical problem, no effective solution has been proposed yet.

SUMMARY

There is provided in embodiments of the present disclosure a method for predicting an optimal exploitation approach for shale oil in-situ conversion, for determining an optimal exploitation approach for shale oil in-situ conversion based on optimal parameters obtained by optimizing key parameters during shale oil in-situ conversion and exploitation, so as to reduce the exploitation cost. The method comprises:

determining a lower limit temperature required for completely converting convertible organic matter in a shale to be measured into oil and gas based on a temperature rise rate and a pre-established relationship between the temperature rise rate and the lower limit temperature required for completely converting the convertible organic matter in the shale into oil and gas; determining an optimal well distance of heating wells, based on a thermal field parameter of a target reservoir of interest, an optimal heating time corresponding to the lower limit temperature, and a pre-established relationship between an optimal well distance of heating wells and the optimal heating time;

determining an oil yield equivalent of a production well in the target reservoir of interest, based on the temperature rise rate and a pre-established relationship between a temperature and an oil yield equivalent of the shale;

determining an effective heating region of a peripheral heating well based on the lower limit temperature; and determining an optimal well pattern, based on a boundary of the effective heating region of the peripheral heating well;

wherein the relationship between the temperature rise rate and the lower limit temperature required for completely converting the convertible organic matter in the shale into oil and gas, the relationship between the well distance of heating wells and the optimal heating time, and the relationship between the temperature and the oil yield equivalent of the shale are pre-established by performing thermal simulation experiments on a plurality of different shale samples in accordance with an in-situ conversion exploitation condition; and the lower limit temperature, the optimal well distance of heating wells, the oil yield equivalent and the optimal well pattern are optimal parameters in the optimal exploitation approach for shale oil in-situ conversion.

There is further provided in embodiments of the present disclosure an apparatus for predicting an optimal exploitation approach for shale oil in-situ conversion. The apparatus comprises:

a lower limit temperature determination unit for determining a lower limit temperature required for completely converting convertible organic matter in a shale to be measured into oil and gas based on a temperature rise rate and a pre-established relationship between the temperature rise rate and the lower limit temperature required for completely converting the convertible organic matter in the shale into oil and gas;

an optimal well distance of heating wells determination unit for determining an optimal well distance of heating wells, based on a thermal field parameter of a target reservoir of interest, an optimal heating time corresponding to the lower limit temperature, and a pre-established relationship between an optimal well distance of heating wells and the optimal heating time;

an oil yield equivalent determination unit for determining an oil yield equivalent of a production well in the target reservoir of interest, based on the temperature rise rate and a pre-established relationship between a temperature and an oil yield equivalent of the shale;

an optimal well pattern determination unit for determining an effective heating region of a peripheral heating well based on the lower limit temperature and determining an optimal well pattern, based on a boundary of the effective heating region of the peripheral heating well;

wherein the relationship between the temperature rise rate and the lower limit temperature required for completely converting the convertible organic matter in the shale into oil and gas, the relationship between the well distance of heating wells and the optimal heating time, and the relationship between the temperature and the oil yield equivalent of the shale are pre-established by performing thermal simulation experiments on a plurality of different shale samples in accordance with an in-situ conversion exploitation condition; and the lower limit temperature, the optimal well distance of heating wells, the oil yield equivalent and the optimal well pattern are optimal parameters in the optimal exploitation approach for shale oil in-situ conversion.

There is further provided in embodiments of the present disclosure a computer device comprising a memory, a processor, and a computer program stored on the memory and executable by the processor, wherein the processor, when executing the computer program, implements the method for predicting an optimal exploitation approach for shale oil in-situ conversion as described above.

There is further provided in embodiments of the present disclosure a computer readable storage medium storing therein a computer program for performing the method for predicting an optimal exploitation approach for shale oil in-situ conversion as described above.

The technical solution provided in the embodiments of the present disclosure achieves the following advantageous technical effects.

Firstly, the relationship between the temperature rise rate and the lower limit temperature required for completely converting the convertible organic matter in the shale into oil and gas, and the relationship between the optimal well distance of heating wells and the optimal heating time are pre-established by performing thermal simulation experiments on a plurality of different shale samples based on an in-situ conversion exploitation condition, so as to solve the problem in the prior art that the lower limit temperature and the optimal well distance of heating wells in the well patterns of different well distances between heating wells. Therefore, based on the relationship between the temperature rise rate and the lower limit temperature as well as the relationship between the optimal well distance of heating wells and the optimal heating time, the optimal parameters, i.e., the lower limit temperature and the optimal well distance of heating wells, can be obtained.

Secondly, the relationship between the temperature and the oil yield equivalent of shale is pre-established by performing thermal simulation experiments on a plurality of different shale samples in accordance with an in-situ conversion exploitation condition, so as to solve the technical problem that the oil and gas yield cannot be optimized in in-situ conversion process due to different temperatures in different regions. Therefore, an optimal parameter, i.e., an oil yield equivalent, can be obtained based on the relationship between temperature and the oil yield equivalent of shale.

In addition, the optimal well pattern is determined based on a boundary of the effective heating region of the peripheral heating well, thereby obtaining an optimal parameter, i.e., an optimal well pattern.

In summary, the technical solution provided in the embodiments of the present disclosure determines an optimal exploitation approach for shale oil in-situ conversion based on optimal parameters obtained by optimizing key parameters during shale oil in-situ conversion and exploitation, thereby reducing the exploitation cost and providing a scientific guidance for shale oil in-situ conversion exploitation.

BRIEF DESCRIPTION OF DRAWINGS

The drawings described here are used for providing further understanding to the present disclosure, and constitute a part of the present application rather than the limitation to the disclosure. In the drawings.

DESCRIPTION OF EMBODIMENTS

In order to more clearly explain purpose, technical solution and advantages of the disclosure, hereinafter the disclosure will be further described in detail in combination with the embodiments and the accompanying drawings. The exemplary embodiments of the disclosure herein and the description thereof are used for explaining the disclosure and do not constitute limitation to the disclosure.

The inventor has found that the prior art related to the shale oil in-situ conversion exploitation merely involves technical solutions proposed from the in-situ conversion method technique itself, and none of these techniques give a method technique for optimizing parameters in the exploitation process. In the process of shale oil in-situ conversion exploitation, many factors and parameters are involved, and the prior art does not involve any technology of how to optimize the parameters and factors, to obtain the optimal parameters, to determine an optimal exploitation approach for shale oil in-situ conversion and to reduce the exploitation cost.

Since the inventor has discovered the above technical problems, in order to overcome the shortcomings existing in the prior art in which parameters in the shale oil in-situ conversion exploitation cannot be optimized, and determination and optimization of key parameters related to shale oil in-situ conversion are lacking, the inventor provides a technical solution of predicting an optimal exploitation approach for shale oil in-situ conversion, in which an optimal exploitation approach for shale oil in-situ conversion can be determined based on optimal parameters obtained by optimizing key parameters during shale oil in-situ conversion and exploitation, so as to reduce the exploitation cost, provide a scientific guidance for shale oil in-situ conversion exploitation, and improve the utilization rate of shale oil resources. Hereinafter the solution of predicting an optimal exploitation approach for shale oil in-situ conversion will be described in detail.

Figure 1:
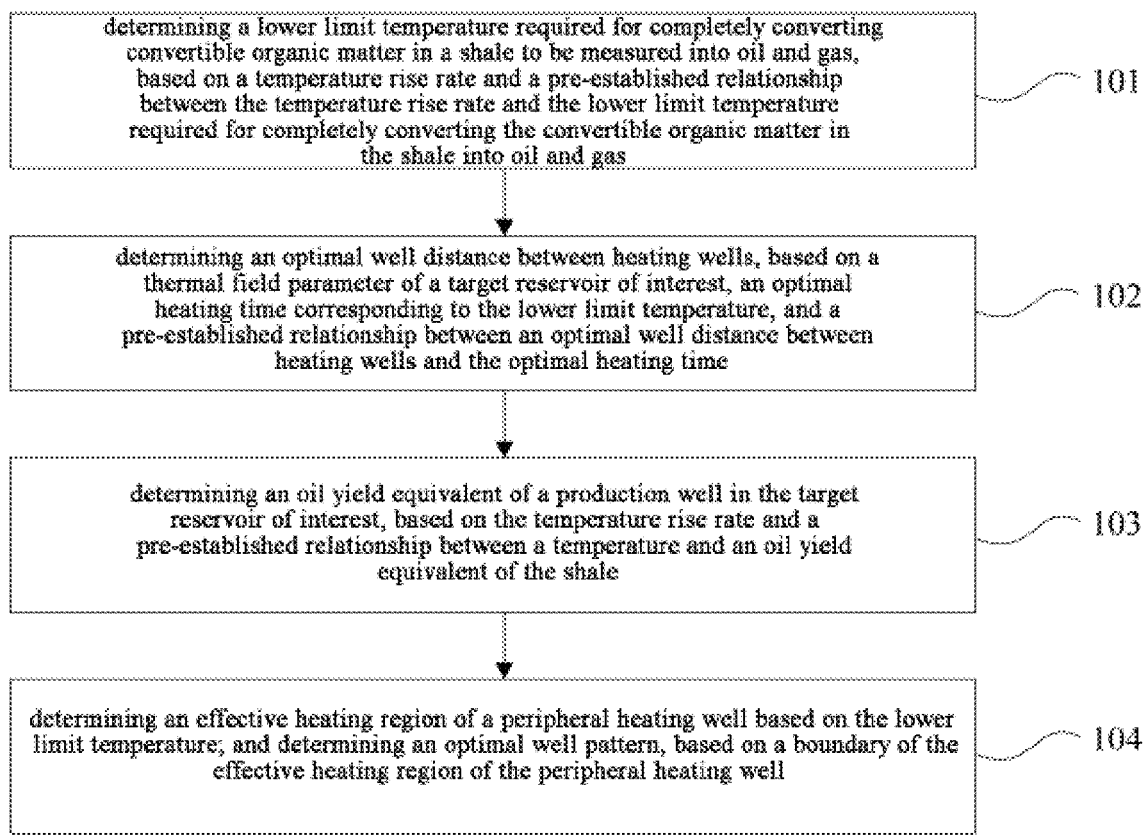
FIG. 1 is a schematic diagram of a flowchart of a method for predicting an optimal exploitation approach for shale oil in-situ conversion according to an embodiment of the present disclosure.
Figure 2A:
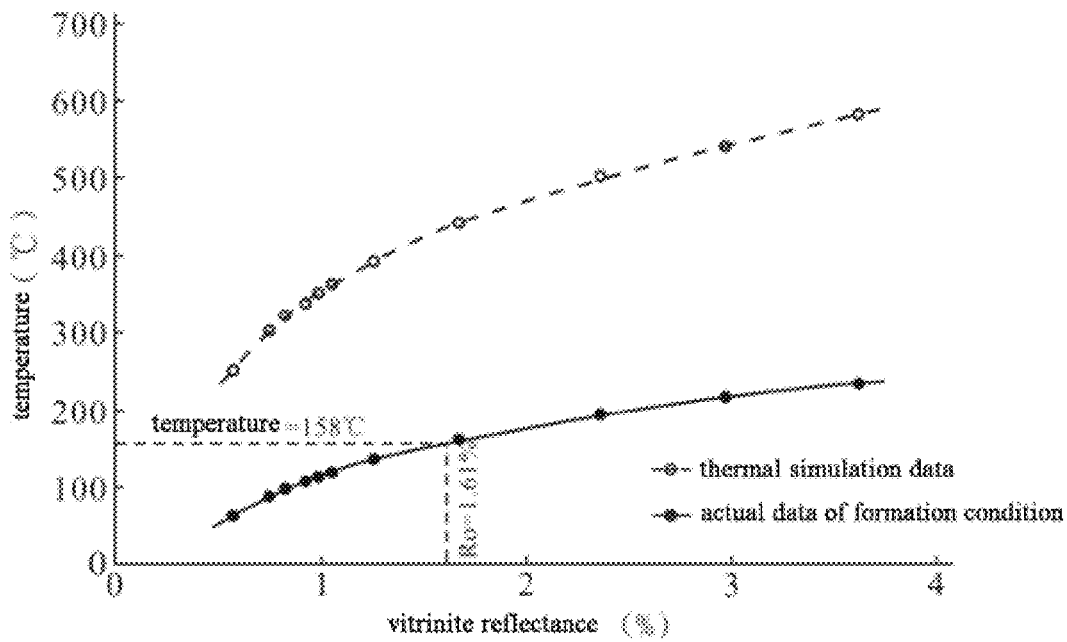
FIGS. 2A and 2B are diagrams showing relations between the in-situ conversion and the temperature, Ro, activation energy of formation conditions during the geological history according to an embodiment of the present disclosure.
Figure 2B:
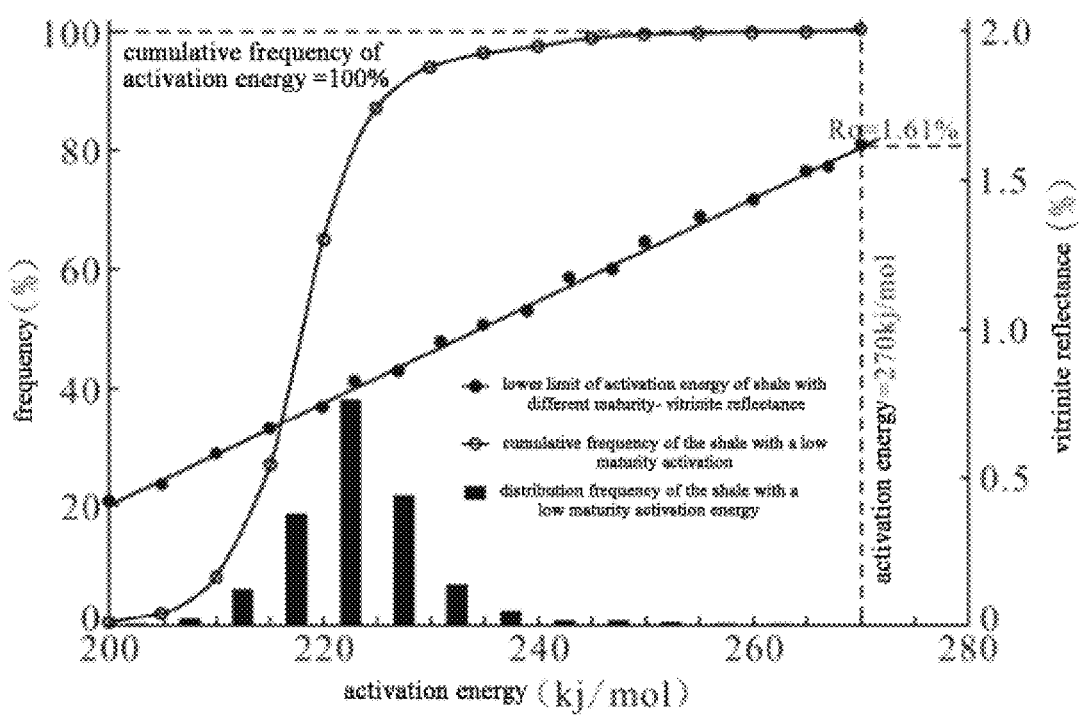
Figure 3:
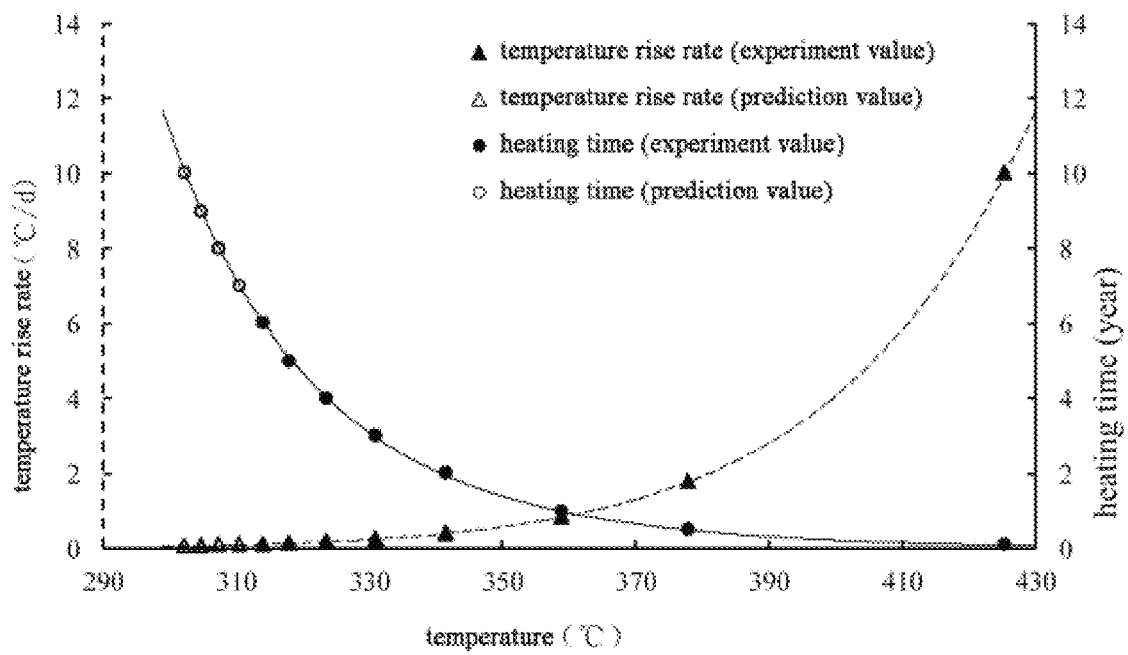
FIG. 3 is a diagram showing a relationship among a temperature, a temperature rise rate and a heating time in in-situ conversion according to an embodiment of the present disclosure.
Figure 4:
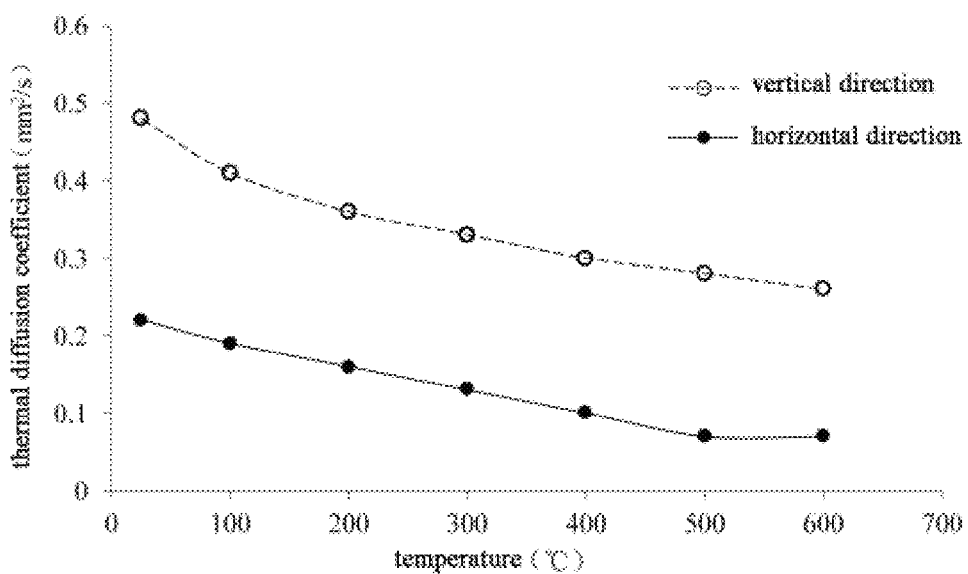
FIG. 4 is a diagram showing a relationship between a thermal diffusion coefficient of shale and a temperature according to an embodiment of the present disclosure.
Figure 5:
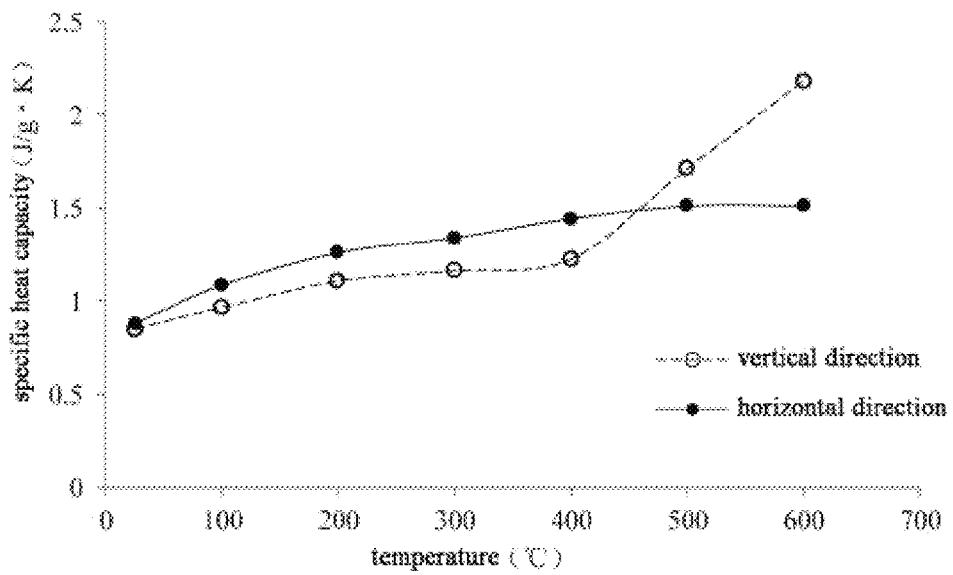
FIG. 5 is a diagram showing a relationship between a specific heat capacity of shale and a temperature according to an embodiment of the present disclosure.
Figure 6:
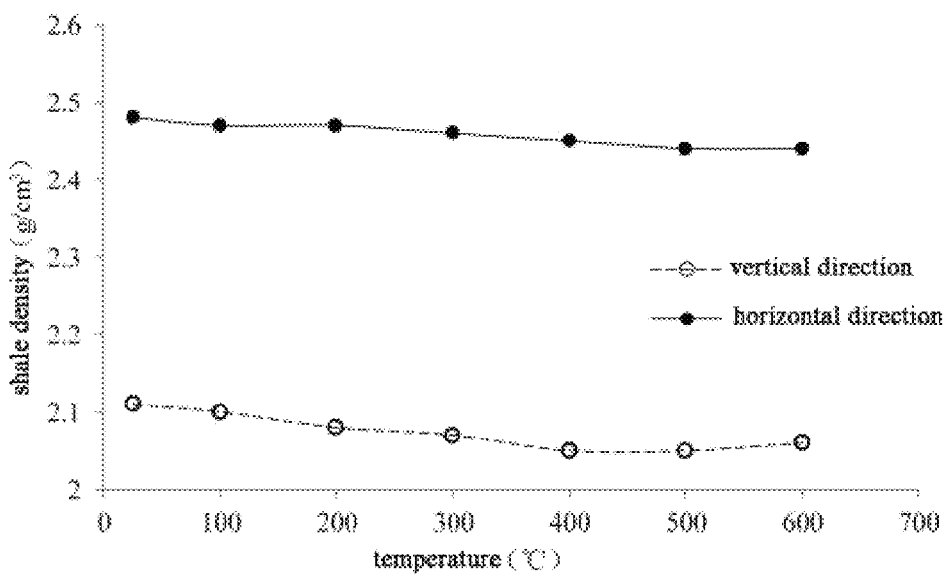
FIG. 6 is a diagram showing a relationship between a shale density and a temperature according to an embodiment of the present disclosure.

FIG. 1 is a schematic diagram of a flowchart of a method for predicting an optimal exploitation approach for shale oil in-situ conversion according to an embodiment of the present disclosure. As shown in FIG. 1, the method comprises the following steps:

a step 101: determining a lower limit temperature required for completely converting convertible organic matter in a shale to be measured into oil and gas based on a temperature rise rate and a pre-established relationship between the temperature rise rate and the lower limit temperature required for completely converting the convertible organic matter in the shale into oil and gas;

a step 102: determining an optimal well distance of heating wells, based on a thermal field parameter of a target reservoir of interest, an optimal heating time corresponding to the lower limit temperature, and a pre-established relationship between an optimal well distance of heating wells and the optimal heating time;

a step 103: determining an oil yield equivalent of a production well in the target reservoir of interest, based on the temperature rise rate and a pre-established relationship between a temperature and an oil yield equivalent of the shale;

a step 104: determining an effective heating region of a peripheral heating well based on the lower limit temperature; and determining an optimal well pattern, based on a boundary of the effective heating region of the peripheral heating well;

wherein the relationship between the temperature rise rate and the lower limit temperature required for completely converting the convertible organic matter in the shale into oil and gas, the relationship between the well distance of heating wells and the optimal heating time, and the relationship between the temperature and the oil yield equivalent of the shale are pre-established by performing thermal simulation experiments on a plurality of different shale samples in accordance with an in-situ conversion exploitation condition; and the lower limit temperature, the optimal well distance of heating wells, the oil yield equivalent and the optimal well pattern are optimal parameters in the optimal exploitation approach for shale oil in-situ conversion.

The technical solution provided in the embodiments of the present disclosure achieves the following advantageous technical effects.

Firstly, the relationship between the temperature rise rate and the lower limit temperature required for completely converting the convertible organic matter in the shale into oil and gas, and the relationship between the optimal well distance of heating wells and the optimal heating time are pre-established by performing thermal simulation experiments on a plurality of different shale samples based on an in-situ conversion exploitation condition, so as to solve the problem in the prior art that the lower limit temperature and the optimal well distance of heating wells in the well patterns of different well distances between heating wells. Therefore, based on the relationship between the temperature rise rate and the lower limit temperature as well as the relationship between the optimal well distance of heating wells and the optimal heating time, the optimal parameters, i.e., the lower limit temperature and the optimal well distance of heating wells, can be obtained.

Secondly, the relationship between the temperature and the oil yield equivalent of shale is pre-established by performing thermal simulation experiments on a plurality of different shale samples in accordance with an in-situ conversion exploitation condition, so as to solve the technical problem that the oil and gas yield cannot be optimized in in-situ conversion process due to different temperatures in different regions. Therefore, an optimal parameter, i.e., an oil yield equivalent, can be obtained based on the relationship between temperature and the oil yield equivalent of shale.

In addition, the optimal well pattern is determined based on a boundary of the effective heating region of the peripheral heating well, thereby obtaining an optimal parameter, i.e., an optimal well pattern.

In summary, the technical solution provided in the embodiments of the present disclosure determines an optimal exploitation approach for shale oil in-situ conversion based on optimal parameters obtained by optimizing key parameters during shale oil in-situ conversion and exploitation, thereby reducing the exploitation cost and providing a scientific guidance for shale oil in-situ conversion exploitation.

Referring now to FIG. 2A to FIG. 18, the steps involved in the method for predicting an optimal exploitation approach for shale oil in-situ conversion are described in detail below.

I. Firstly, the steps of establishing the models in advance according to the thermal simulation experiment are introduced.

1. Firstly, the steps of establishing a relationship (for example, a model for predicting a lower limit temperature) between the temperature rise rate and the lower limit temperature required for completely converting the convertible organic matter in the shale into oil and gas are introduced.

The shale samples in the target reservoir of interest are collected, to acquire a lower limit temperature required for completely converting the convertible organic matter in the shale into oil and gas under different temperature rise rate conditions by performing thermal simulation experiments in accordance with the in-situ conversion exploitation condition, to establish a model for evaluating the lower limit temperature (a model for predicting a lower limit temperature) required for completely converting the convertible organic matter in the shale into oil and gas under different temperature rise rate conditions.

The reason why the model for predicting a lower limit temperature is established based on the temperature rise rate is described as follows: the rate at which the organic matter is converted into oil and gas in shale is related to the activation energy, temperature and time of organic matter, which conforms to the first order equation of reaction kinetics. During the evolution of geological history under stratigraphic conditions, the rate at which the organic matter is converted into oil and gas is exponentially related to temperature, and linearly related to the time experienced. In the exploitation of shale oil with the in-situ conversion technology, the formation temperature in-situ conversion is much higher than a minimum temperature required for completely converting the convertible organic matter in the shale into oil and gas during the geological history period. The analysis of kerogen shale samples of type I and type II in many oil and gas-bearing basins around the world reveals that a lower limit of activation energy of core samples with different maturities is positively correlated with the corresponding vitrinite reflectance (Ro). The frequency of activation energy distribution for shale with a low maturity is similar to normal distribution, the cumulative frequency of activation energy for the shale with a low maturity 100% corresponds to about 270 kJ/mol, that is, the maximum activation energy is about 270 kJ/mol, and the temperature required for converting corresponding organic matter into oil and gas is about 158° C. which is an upper limit temperature for liquid hydrocarbon generation, and the corresponding vitrinite reflectance is about 1.61%. The final temperature required for the in-situ conversion of shale oil exceeds 300° C. (FIG. 2A and FIG. 2B), which is far higher than the upper limit temperature for completely converting the convertible organic matter into oil and gas in the shale during geological history, and also far higher than start reaction temperature at which the maximum activation energy of the convertible organic matter in shale correspondingly generates oil and gas, and thus, the inventor has found that the oil and gas generation rate is related to the temperature rise rate under the shale in-situ conversion conditions. Due to the discovery of the technical problem, the inventor proposes the model for predicting a lower limit temperature is established based on the temperature rise rate. The thermal simulation experiment performed on the shale samples is introduced as below.

Multiple groups of organic matter-rich shale samples having low maturity are collected in the target reservoir of interest, for example, multiple groups of organic matter-rich shale samples having low maturity are collected from 7 long sections of the Ordos Basin, are pulverized and then mixed uniformly to be divided into 7 parts, each of which is heavier than 3 kg. For the accuracy and reliability of thermal simulation experiments, kerogen shale samples of type I and type II with vitrinite reflectance (Ro) less than 0.7% are preferably used. Shale samples having a total organic carbon content (TOC) of more than 5% of the shale are preferably used. Multiple groups of collected shale samples are preferably pulverized and mixed uniformly. The sample is pulverized to 40 to 100 mesh, preferably 60 mesh.

According to the exploitation conditions of shale oil in-situ conversion, thermal simulation experiments are carried out to simulate the temperature rise rate corresponding to different exploitation time of 0.1 to 6 years in-situ conversion. Thermal simulation is carried out for each shale sample in a semi-open system, in which the simulated in-situ exploitation time comprises 0.1 year, 0.5 year, 1 year, 2 year, 3 year, 4 year, 5 year and 6 year, respectively, and the corresponding temperature rise rates are 10° C./d, 1.797° C./d, 0.847° C./d, 0.399° C./d, 0.257° C./d, 0.187° C./d, 0.147° C./d, 0.121° C./d, respectively. According to the pressure conditions of the shale oil in-situ conversion exploitation, the heat simulation preset fluid pressure is 1 MPa to 10 MPa, preferably 1 MPa, and the hydrocarbon removal pressure is 2 MPa to 15 MPa, preferably 3 MPa. When the cumulative oil equivalent produced in the simulation process is greater than 98%, preferably greater than 99%, of the final oil yield equivalent, that is, the lower limit temperature required for completely converting the convertible organic matter in the shale into oil and gas is adopted. Thermal simulation experiment proves that the rate at which the organic matter in shale is converted into oil and gas through thermal cracking is well correlated with the temperature rise rate, and increases with the increase of the temperature rise rate.

In the process of shale oil in-situ conversion and exploitation, the well distance of heating wells are different, and the heating wells need different time to reach the lower limit temperature required for completely converting the convertible organic matter into oil and gas, that is, the temperature rise rates are different. The temperature rise rate is a key parameter in the in-situ conversion exploitation, and based on the thermal simulation data, a model for evaluating the lower limit temperature (a model for predicting a lower limit temperature) required for completely converting the convertible organic matter in the shale into oil and gas is established by utilizing the temperature rise rate (equation (1)) (FIG. 3):

$$T_{end} = a_1 \times TR^{b_1} \tag{1}$$

In the equation, $T_{end}$ denotes the lower limit temperature required for completely converting the convertible organic matter in the shale into oil and gas, ° C.; TR denotes the temperature rise rate, ° C./d; and $a_1$, $b_1$ denote empirical coefficients, which may be 363.201, 0.06867, respectively.

In a specific implementation, in the embodiment of the present disclosure, the above described lower limit temperature may also be refer to as the optimal heating temperature required for completely converting the convertible organic matter in shale into oil and gas.

2. Secondly, the steps of establishing the relationship between the optimal well distance of heating wells and the optimal heating time (for example, the optimal well distance of heating wells model) are introduced.

According to the thermal simulation experiment data, dynamic thermal field parameters varying with temperature are obtained, a dynamic thermal field parameter evaluation model is established, and the optimal well distance of heating wells model is established by using the thermal field simulation data and the conditions of different well distances between heating wells.

In an embodiment, the relationship between the optimal well distance of heating wells and the optimal heating time may be pre-established according to the following process:

establishing a relationship between a thermal diffusion coefficient and a temperature based on thermal diffusion coefficients at different temperature points that are measured by a laser thermal conductivity instrument in a process of a thermal simulation experiment;

establishing a relationship between a specific heat capacity and a temperature based on specific heat capacities at different temperature points that are measured by a simultaneous thermal analyzer in a process of a thermal simulation experiment;

establishing a relationship between a shale thermal conductivity and a temperature based on shale densities at different temperature points that are measured by a thermal dilatometer in a process of a thermal simulation experiment; and establishing a relationship between the optimal well distance of heating wells and the optimal heating time, by determining, through thermal field simulation, various optimal heating time with which all the effective heating regions of the shale reach the lower limit temperature under a condition of various well distances of heating wells, based on the relationship between the thermal diffusion coefficients and the temperature, the relationship between the specific heat capacity and the temperature, and the relationship between the shale thermal conductivity and the temperature.

In a specific implementation, the affecting thermal field parameters mainly include thermal diffusion coefficients, the specific heat capacity and the thermal conductivity. The thermal field parameters in the vertical direction and in the horizontal direction are measured respectively due to large difference in heterogeneity between the vertical direction and the horizontal direction of the shale. During in-situ conversion exploitation, the formation temperature changes greatly, and the thermal field parameters change greatly with the temperature, therefore, it is necessary to measure the dynamic thermal field parameters under different temperature conditions. Target shale samples in the research region are collected. Hereinafter the process of establishing the relationship between the thermal diffusion coefficients and the temperature, the relationship between the specific heat capacity and the temperature, and the relationship between the shale thermal conductivity and the temperature will be introduced.

(1) Firstly, according to the national standard GB/T22588-2008, the thermal diffusion coefficients at different temperature points are measured by a laser thermal conductivity instrument, and the relationship between the thermal diffusion coefficients and the temperature is established according to the measured data, such as a model that the thermal diffusion coefficients vary with the temperature (equation (2), equation (3)) (FIG. 4), and the relationship between the thermal diffusion coefficients and the temperature comprises a model for predicting a thermal diffusion coefficient in a vertical direction and a model for predicting a thermal diffusion coefficient in a horizontal direction.

The model for predicting a thermal diffusion coefficient in the vertical direction is shown as below (equation (2)):

$$\alpha_v = a_2 \ln(T) + b_2 \tag{2}$$

In the equation, $\alpha_v$ denotes a thermal diffusion coefficient in the vertical direction, mm²/s; T denotes temperature, ° C.; and $a_2$, $b_2$ denote empirical coefficients, which may be −0.069022, 0.714776, respectively.

The model for predicting a thermal diffusion coefficient in the horizontal direction is shown as below (equation (3)):

$$\alpha_h = a_3 e^{b_3 T} \tag{3}$$

In the equation, $a_h$ denotes a thermal diffusion coefficient in the horizontal direction, mm²/s; T denotes temperature, ° C.; and $a_3$, $b_3$ denote empirical coefficients, which may be 0.23755, −0.00217, respectively.

(2) Secondly, according to the United States Standard ASTM E 1269-11, the specific heat capacity at different temperature points is measured by the simultaneous thermal analyzer, and the relationship between the specific heat capacity and the temperature is established according to the measured data, such as a model of the specific heat capacity varying with the temperature (equation (4), equation (5)) (FIG. 5), and the relationship between the specific heat capacity and the temperature comprises a model for predicting the specific heat capacity in the vertical direction and a model for predicting the specific heat capacity in the horizontal direction.

The model for predicting the specific heat capacity in the vertical direction is shown as below (equation (4)):

$$Cp_v = a_{41} T^3 + a_{42} T^2 + a_{43} T + b_4 \tag{4}$$

In the equation, $Cp_v$ denotes a hot melt ratio in the vertical direction, J/g·K; T denotes temperature, ° C.; and $a_{41}$, $a_{42}$, $a_{43}$, $b_4$ denote empirical coefficients, which may be 0.0000000148, −0.0000095079, 0.002748573, 0.78690397, respectively.

The model for predicting the specific heat capacity in the horizontal direction is shown as below (equation (5)):

$$Cp_h = a_5 \ln(T) + b_5 \tag{5}$$

In the equation, $Cp_h$ denotes specific heat capacity in the horizontal direction, J/g·K; T denotes temperature, °C.; and $a_5$, $b_5$ denote empirical coefficients, which may be 0.2095, 0.1703, respectively.

Figure 7:
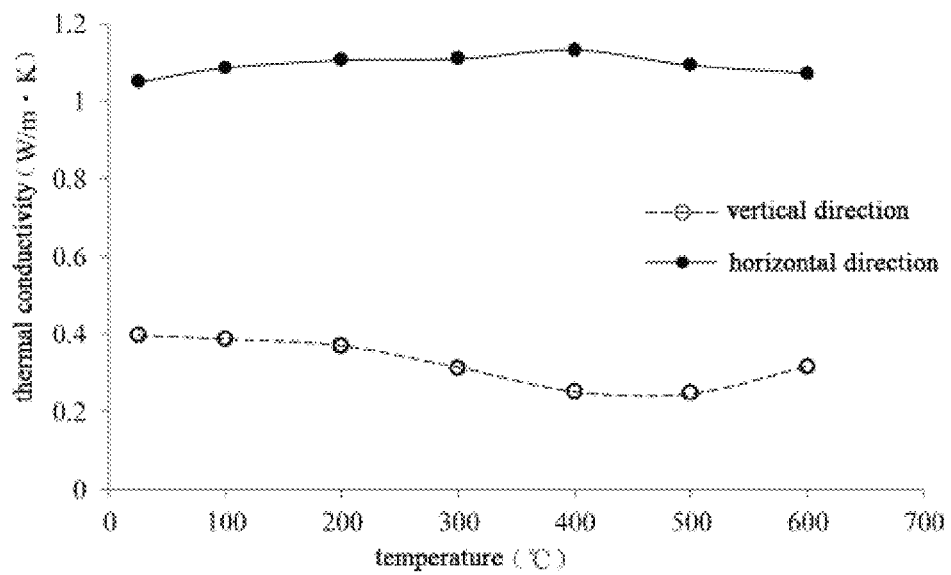
FIG. 7 is a diagram showing a relationship between a thermal conductivity of shale and a temperature according to an embodiment of the present disclosure.
Figure 8:
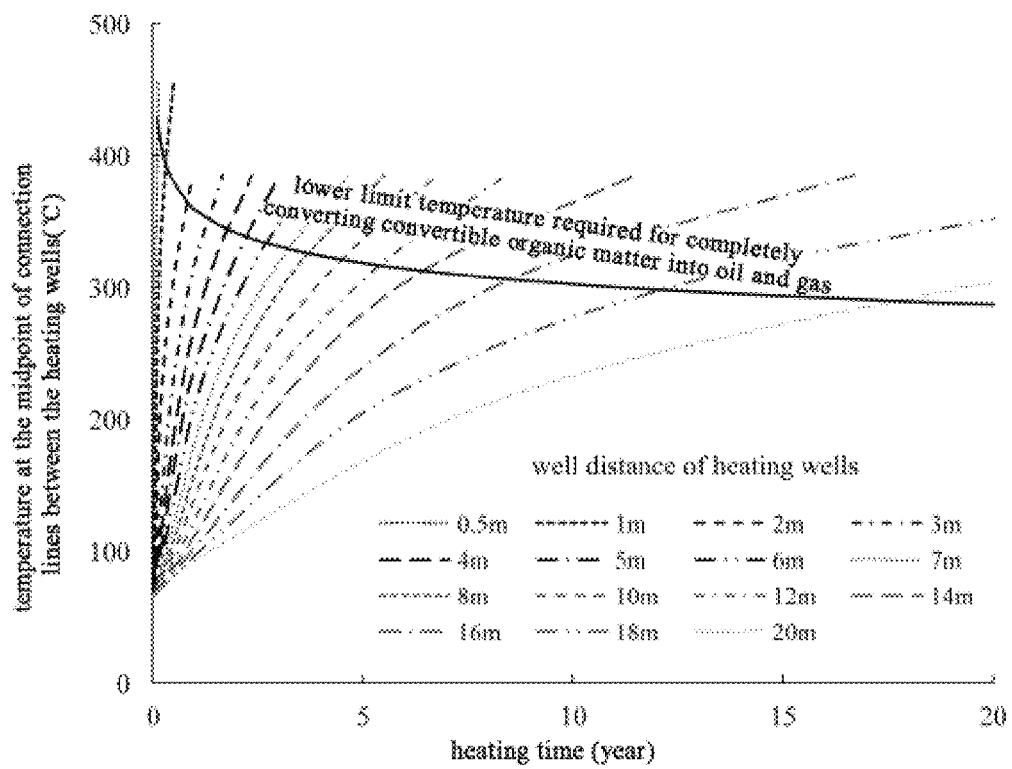
FIG. 8 is a diagram showing a relationship between a heating time and a temperature at a center of the connection line between heating wells in shale in-situ conversion according to an embodiment of the present disclosure.
Figure 9:
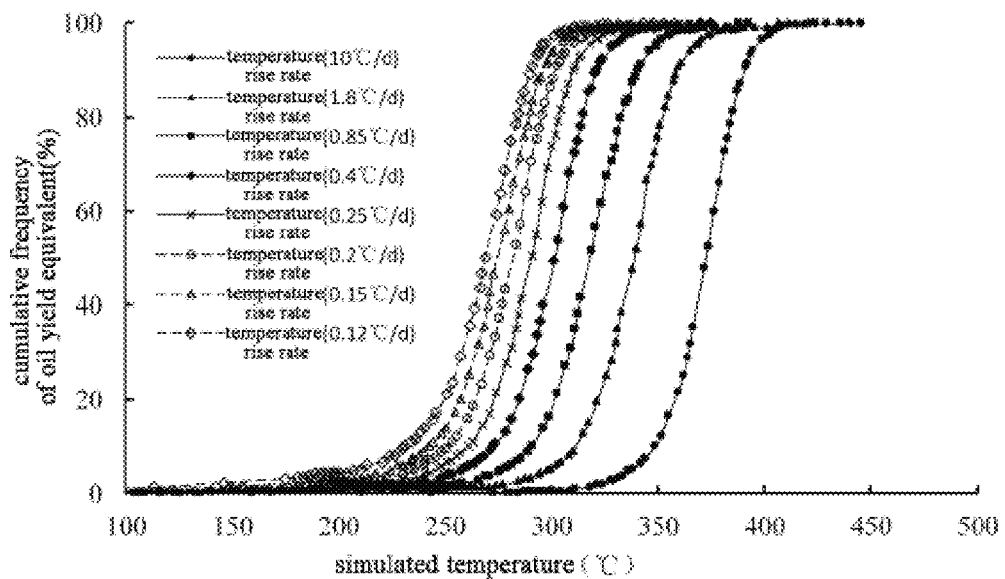
FIG. 9 is a diagram showing a relationship between a cumulative frequency of oil yield equivalent and a simulated temperature in shale in-situ conversion according to an embodiment of the present disclosure.
Figure 10:
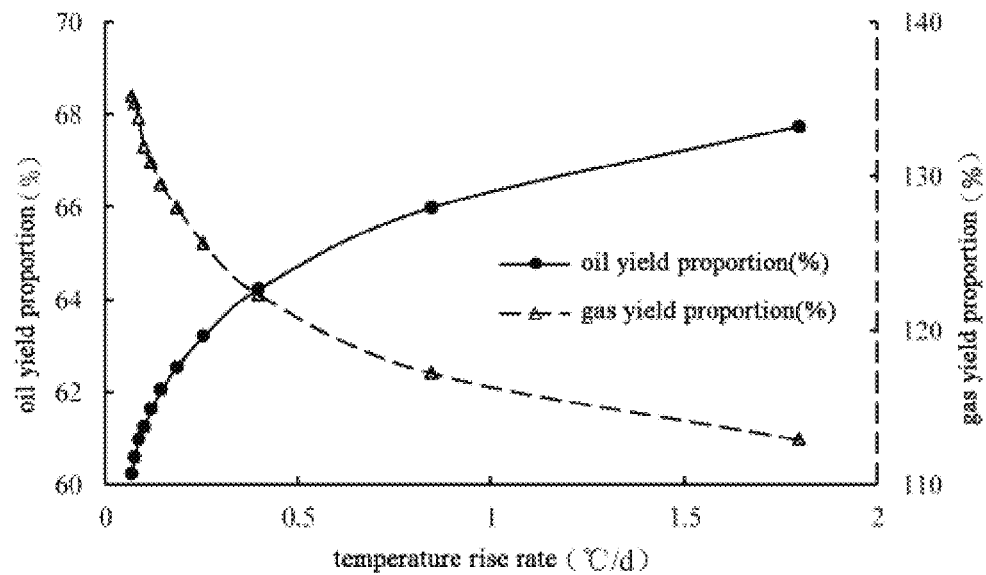
FIG. 10 is a diagram showing a relationship between a temperature rise rate and a ratio of oil and gas yield in shale in-situ conversion according to an embodiment of the present disclosure.

(3) Next, according to the national standard GB/T 23561.2-2009, the shale density at different temperature points is measured using a thermal expansion instrument (FIG. 6), and the thermal conductivity of the shale is calculated according to equation (6), i.e., the relationship between the shale thermal conductivity and the temperature is established, such as a model for predicting a shale thermal conductivity (equation (6), FIG. 7).

$$\lambda = a \times Cp \times \rho \tag{6}$$

In the equation, $\lambda$ denotes thermal conductivity, W/m·K; T denotes temperature, °C.; a denotes the thermal diffusion coefficient (the thermal diffusion coefficients in the vertical direction or in the horizontal direction that can be obtained according to the above equation (2) or (3)), mm²/s; Cp denotes the specific heat capacity (the specific heat capacity in the vertical direction or in the horizontal direction that can be obtained according to the above equation (4) or (5)), J/g·K; ρ denotes a shale density, g/cm³. Based on the thermal diffusion coefficients and the specific heat capacity in the vertical direction or in the horizontal direction, the thermal conductivity in the vertical direction or in the horizontal direction can be obtained.

The process of establishing the relationship between the optimal well distance of heating wells and the optimal heating time is described as below.

According to the acquired thermal field parameters of the target reservoir of interest, the heating time when shale effective heating regions all reach the lower limit temperature required for completely converting the convertible organic matter in shale into oil and gas in different well distances between heating wells conditions, that is, the optimal heating time (FIG. 8), is determined by thermal field simulation. The optimal heating time can ensure that the convertible organic matter in the shale is completely converted into oil and gas and is produced without causing waste of thermal energy due to additional heating. Due to factors such as heater life or the like, heating time cannot be too long. In addition, the greater the well distance of heating wells is, the longer the heating time required is, the more serious the waste of thermal energy is, and the higher the exploitation cost is, so that determination of reasonable well pattern and optimum heating time can reduce the in-situ conversion exploitation cost and save thermal energy. Therefore, the relationship between the optimal well distance of heating wells and the optimal heating time is established.

The relationship between the optimal well distance of heating wells and the optimal heating time (for example, the model for predicting an optimal well distance of heating wells) is determined by the equation (7):

$$t_{Oh} = f(\lambda) \begin{cases} a_{71} L_{hw} + b_{71} & L_{hw} < 8m \\ a_{72} L_{hw}^3 + a_{73} L_{hw}^2 + a_{74} L_{hw} + b_{72} & L_{hw} \geq 8m \end{cases} \tag{7}$$

In the equation, $t_{oh}$ denotes the optimal heating time of the heating well, $L_{hw}$ denotes the well distance between heating wells, $f(\lambda)$ denotes a ratio of a measured value of the thermal conductivity of shale sample to be measured to a calculated value, $f(\lambda)$ differs in the vertical direction and in the horizontal direction, respectively, and the calculated value is determined according to the thermal diffusion coefficient and the specific heat capacity in the vertical direction or in the horizontal direction (see the above description); and $a_{71}$, $b_{71}$, $a_{72}$, $a_{73}$, $a_{74}$, $b_{72}$ denote empirical coefficients, which may be 0.4756, −0.1477, 0.0116, −0.3738, 4.3719, −13.387, respectively.

3. Next, the introduction is given as to establishment of a model for evaluating the oil yield equivalent with the temperature (the relationship between temperature and the oil yield equivalent of shale, such as a model for predicting an oil yield equivalent) based on the oil yield equivalent at different temperature rise rates that are obtained through thermal simulation, and a model for evaluating the oil and gas yield ratio with the temperature rise rate (a model for predicting a ratio of oil and gas yield).

A model for evaluating an oil yield equivalent (the oil yield equivalent prediction model) is established by utilizing data of the oil yield equivalent by shale thermal simulation in different temperature rise rate conditions of the target reservoir of interest:

$$RQ_{BOE} = \Delta T \times ((a_8 ST + b_8) ST + c_8) + RQ_{50} \tag{8}$$

wherein, $\Delta T = |T - T_{50}|$;
ST = Sin(ln(ΔT));

In the equation, $RQ_{BOE}$ denotes a ratio of a cumulative oil yield equivalent corresponding to a temperature to a total cumulative oil yield equivalent, %; T denotes a temperature corresponding to a preset cumulative oil yield equivalent, °C.; $T_{50}$ a temperature corresponding to 50% of the total cumulative oil yield equivalent, in unit of °C.; $RQ_{50}$ denotes a ratio of a cumulative oil yield equivalent corresponding to the temperature $T_{50}$, %; $a_8$, $b_8$, $c_8$ denote empirical coefficients, and different temperature rise rates have different values (as shown in the Table 1 below).

TABLE 1

Values of the empirical coefficients $a_8$, $b_8$, $c_8$ under different temperature rise rate conditions

| Temperature Rise Rate | $RQ_{50} < 50\%$ | | | $RQ_{50} \geq 50\%$ | | |
| --- | --- | --- | --- | --- | --- | --- |
| (°C./d) | $a_8$ | $b_8$ | $c_8$ | $a_8$ | $b_8$ | $c_8$ |
| 0.12 | 0.1597 | −0.7642 | −1.4609 | −0.517 | 0.72603 | 1.7554 |
| 0.147 | 0.3686 | −0.7049 | −1.6637 | −0.28574 | 0.9077 | 1.64618 |
| 0.187 | 0.356 | −0.6799 | −1.5938 | −0.20897 | 1.04635 | 1.76677 |
| 0.256 | 0.3237 | −0.6985 | −1.5596 | −0.2206 | 1.07021 | 1.83072 |
| 0.4 | 0.2671 | −0.7588 | −1.5544 | −0.23542 | 1.06699 | 1.85918 |
| 0.85 | 0.2862 | −0.8021 | −1.6468 | −0.30024 | 0.85298 | 1.68964 |
| 1.797 | 0.3273 | −0.7643 | −1.6516 | −0.17539 | 1.02439 | 1.74198 |
| 10 | 0.2373 | −0.9237 | −1.7211 | −0.24402 | 1.05795 | 1.81099 |

The model for predicting a ratio of oil and gas yield is established by utilizing the oil yield produced by shale thermal simulation, and the gas yield data in different temperature rise rate conditions of the target reservoir of interest (FIG. 10):

$$RQ_{gas} = a_9 \ln(TR) + b_9 \tag{9}$$

$$RQ_{oil} = a_{10} TR^{b_{10}} \tag{10}$$

In the equation, $RQ_{gas}$ denotes a ratio of produced hydrocarbon gas to the hydrocarbon gas produced by an aluminum thermal simulation method (FA), %; $RQ_{oil}$ denotes a ratio of oil yield to the oil yield produced by the aluminum thermal simulation method (FA), %; $a_9$, $b_9$, $a_{10}$, $b_{10}$ denote empirical coefficients, which may be −6.9804, 116.2995, 66.3624, 0.0355, respectively. By the aluminum thermal simulation method (FA), the oil and gas yield of the shale sample in the target reservoir of interest can be obtained.

4. Next, introduction is given to establishment of the relationship between the cumulative input energy of the heater and the heating time, such as a model for predicting heater cumulative input energy, by utilizing the thermal field simulation data based on the heater surface temperature to be kept constant and the thermal field propagation rate kept to be constant.

Figure 11:
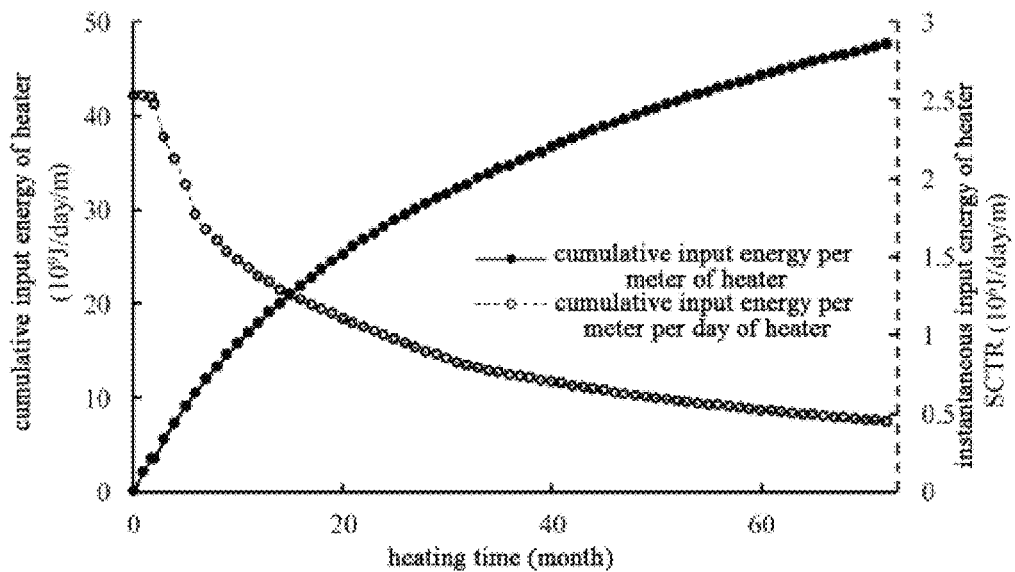
FIG. 11 is a diagram showing a relationship among transient input energy of a heater, cumulative input energy of a heater, and a heating time in shale in-situ conversion according to an embodiment of the present disclosure.

When the shale is converted and heated in situ, the surface temperature of heater is kept constant. According to the constant thermal field propagation rate, the instantaneous input energy of the heater decreases gradually with the increasing of the heating time and the rising of formation temperature. The cumulative input energy and the instantaneous input energy of the heater are obtained by the thermal field simulation. The cumulative input energy of the heater is preferably the cumulative input energy of the heater per meter, and the instantaneous input energy of the heater is preferably the input energy of the heater per meter per day, and a model for evaluating the input energy of the heater with the heating time (FIG. 11).

The model for predicting heater instantaneous input energy (equation (11)):

$$E_{instant} = \begin{cases} a_{111}e^{b_{111}t} & t < 6 \\ a_{112}\ln(t) + b_{112} & t \geq 6 \end{cases} \quad (11)$$

In the equation, $E_{instant}$ denotes instantaneous input energy required at the corresponding heating time t of the heater, J; t denotes the heating time, month; $a_{111}$, $b_{111}$, $a_{112}$, $b_{112}$ denote empirical coefficients, which may be 2.8913, −0.0791, −0.5320, 2.6870, respectively.

The a model for predicting heater cumulative input energy (equation (12)):

$$E_{cum} = \sum_{i=1}^{n}\sum_{j=1}^{m} E_{instant\_ij} \quad (12)$$

In the equation, $E_{instant\_ij}$ denotes the instantaneous input energy of the heater on the jth day in the ith month, J; $E_{cum}$ denotes the cumulative input energy of the heater in the nth month, J; n denotes the cumulative heating time of the heater, month; and m denotes the number of days of the ith month, day.

5. Next, introduction is given as to pre-establishment of the relationship between the well distance of heating wells and a completely converted volume ratio of the convertible organic matter in the development well group (a prediction model of the completely converted volume ratio of the convertible organic matter in the development well group), the relationship among the well distance between heating wells, the number of layers in the well pattern and a recovery ratio of the recoverable oil equivalent within the development well group (a model for predicting a recovery ratio of recoverable oil equivalent), as well as the steps of improving utilization rate of recoverable oil and gas resources to the maximum extent by utilizing the prediction model of the completely converted volume ratio of the convertible organic matter in the development well group and the pre-established model for predicting a recovery ratio of recoverable oil equivalent, on the basis of ensuring the optimal exploitation approach for shale oil in-situ conversion.

Based on the shale temperature rise rate, the thermal field distribution, the oil and gas yield and the optimal well pattern, a relationship between the well distance of heating wells and a completely converted volume ratio of the convertible organic matter in the development well group, such as the prediction model of the completely converted volume ratio of the convertible organic matter in the development well group within the development well group, and a relationship between the well distance between heating wells, the number of layers in the well pattern and a recovery ratio of the recoverable oil equivalent within the development well group, such as the model for predicting a recovery ratio of recoverable oil equivalent, are established, so as to acquire the utilization rate of recoverable oil and gas, to improve utilization rate of recoverable oil and gas resources to the maximum extent on the basis of ensuring the optimal exploitation approach for shale oil in-situ conversion.

The utilization rate of recoverable oil and gas under different well distances between heating wells conditions is determined based on the thermal field distribution, the temperature rise rate, the oil and gas yield and the optimal well pattern. The utilization rate of recoverable oil and gas refers to the percentage in-situ converted oil yield equivalent to the total recoverable oil equivalent within the plane projection range of the effective heating region under in-situ conversion exploitation conditions.

When a vertical well pattern is adopted for the heating wells, the utilization rate of resources in the effective heating region of a development well group is 100%.

Figure 12:
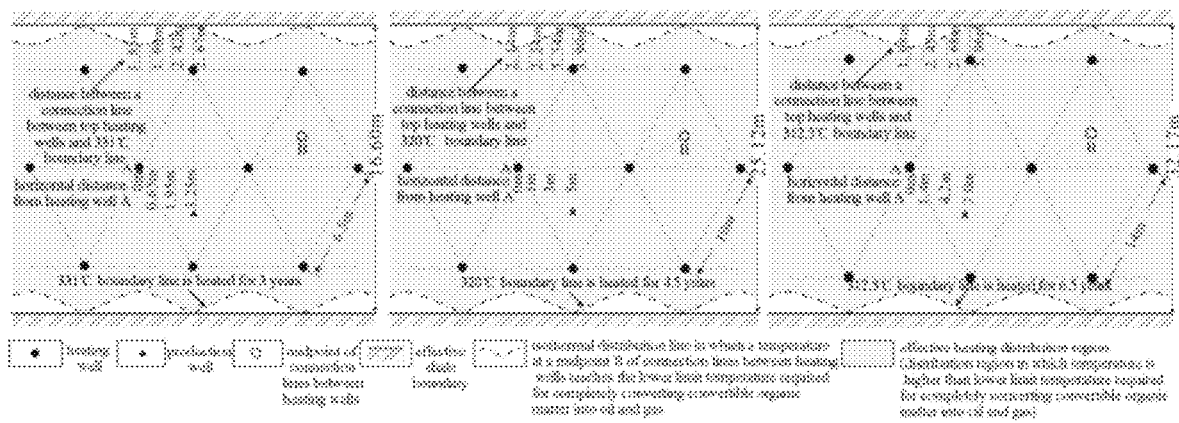
FIG. 12 is a diagram showing a distribution of effective heating regions with different well distances between heating wells in a horizontal well pattern of heating wells for shale in-situ conversion according to an embodiment of the present disclosure.
Figure 13:
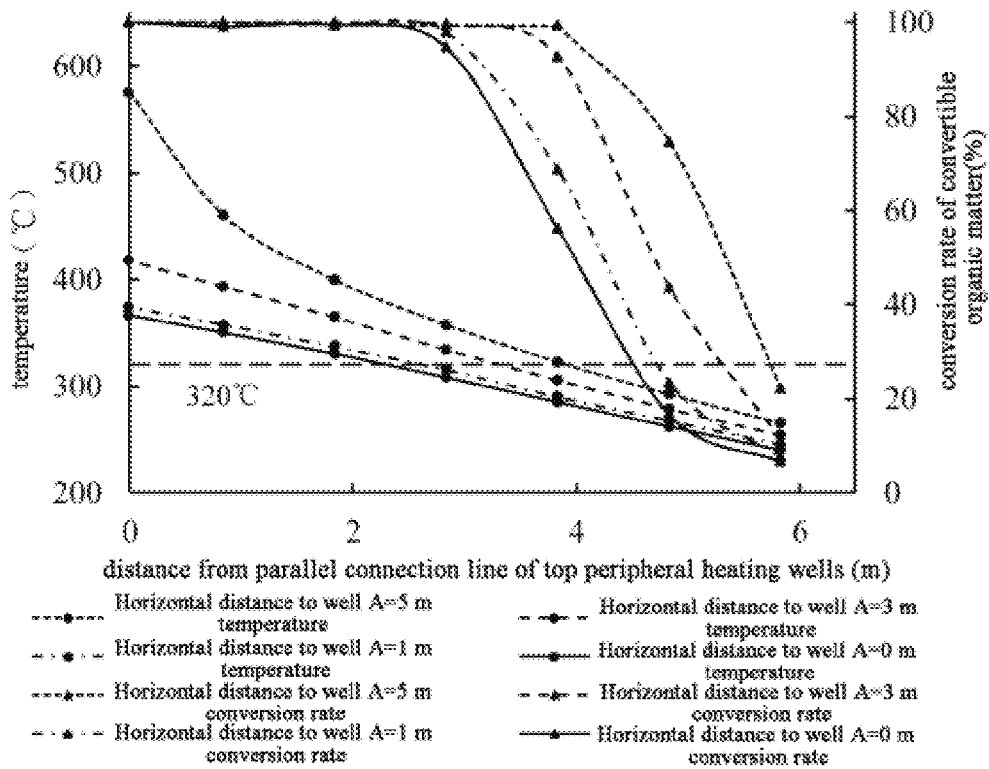
FIG. 13 is a diagram showing a relationship between a distance above the parallel connection lines of the heating wells at the periphery of the top layer, a temperature, and a conversion rate of convertible organic matter, in a horizontal well pattern of heating wells for shale in-situ conversion with a well distance of heating wells of 10 m according to an embodiment of the present disclosure.
Figure 14:
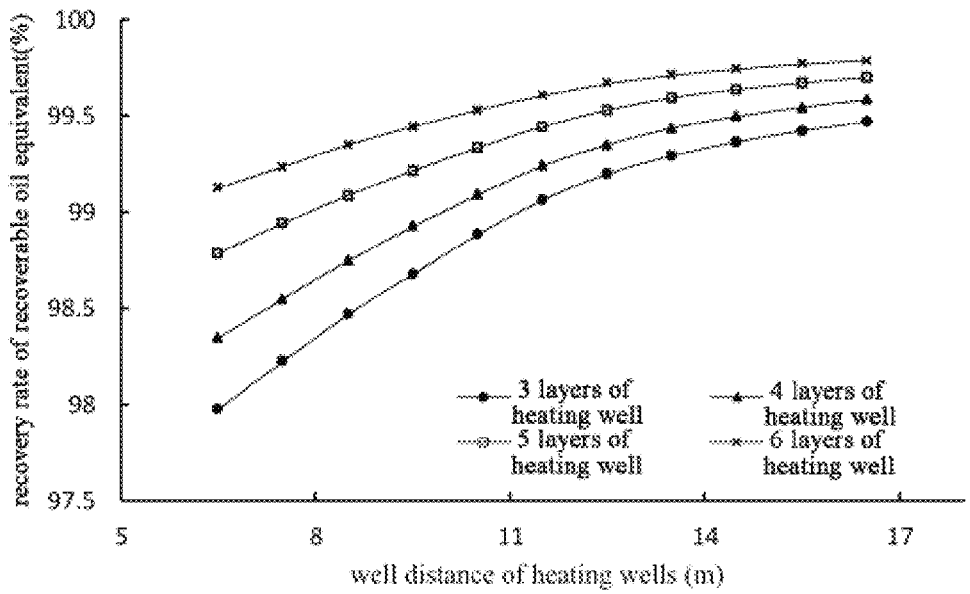
FIG. 14 is a diagram showing a relationship between a well distance of heating wells and a recoverable ratio of recoverable oil equivalent, in a horizontal well pattern of heating wells for shale in-situ conversion according to an embodiment of the present disclosure.

When a horizontal well pattern is adopted for the heating wells, at the end of heating, because the temperature of some areas between the upper and lower peripheral wells and the boundary of the effective shale cannot reach the lower limit temperature required for completely converting the convertible organic matter into oil and gas, the utilization rate of oil and gas resources in some areas is less than 100%. For example, when the heating wells are 10 meters away and arranged in three layers, the optimal distance between the top heating well and the effective shale top boundary and between the bottom heating well and the effective shale bottom boundary is 3.9 meters, the heating wells are heated for 4.5 years to reach 320° C., i.e., the lower limit temperature required for completely converting the convertible organic matter into oil and gas, the outermost boundary of the effective heating region outside the top and bottom heating wells reaches 3.9 meters, at this time the temperature and the conversion rate of the convertible organic matter at different distances above and below the top and bottom heating wells in the horizontal direction of Well A in FIG. 12 are greatly different. The effective shale regions between the top heating wells and the effective shale top boundary and between the bottom heating wells and the effective shale bottom boundary cannot all reach the lower limit temperature required for completely converting the convertible organic matter in shale into oil and gas, and the resource utilization ratio cannot reach 100% (see FIG. 13).

The completely converted volume ratio of the convertible organic matter in the development well group refers to a ratio of a volume of the convertible organic matter that totally becomes to oil and gas within a plane projection area of the effective heating region to a volume of the effective shale within the plane projection area of the effective heating region, when the temperature at center of the connection line between the heating wells reaches the lower limit temperature of completely converting the convertible organic matter within one in-situ conversion exploitation well group. Based on the simulation data of thermal field distribution, the prediction model of the completely converted volume ratio of the convertible organic matter in the development well group is established by utilizing the well distance of heating wells in a exploitation unit in the horizontal well pattern of the heating wells (equation (13)).

$$RUV = 100 - \begin{cases} a_{131}L_{hw}^{b_{131}} + c_{131}\ln(L_{hw}) + d_1 & L_{hw} \leq 10m \\ a_{132}L_{hw}^{b_{132}} + c_{132}L_{hw} & L_{hw} > 10m \end{cases} \quad (13)$$

In the equation, RUV denotes the completely converted volume ratio of the convertible organic matter in the development well group, %; $L_{hw}$ denotes the well distance between heating wells, m; $a_{131}$, $b_{131}$, $c_{131}$, $d_{131}$, $a_{132}$, $b_{132}$, $c_{132}$ denote empirical coefficients, which may be 0.149, −1.0337, 0.1499, −0.3619, 0.0711, −2.431, 0.5645, −0.841, respectively.

In an embodiment of the present disclosure, the completely converted volume ratio of the convertible organic matter in the development well group can be obtained also by the equation (14).

$$UE = 100 - RUV \quad (14)$$

In the equation, UE denotes the completely converted volume ratio of the convertible organic matter in the development well group, %.

The effective shale thickness and the well distance of heating wells are different, and the number of layers in the well pattern differs for the horizontal heating wells, in consideration of the well distance of heating wells and the number of well distance of heating wells layers, the model for predicting a recovery ratio of recoverable oil equivalent within one exploitation well group in the optimal well pattern is acquired in the condition of different number of well distance of heating wells layers and different well distances between heating wells when the temperature at center of the connection line between the heating wells reaches the lower limit temperature of completely converting the convertible organic matter, by the equation (15) (equation (15)) (FIG. 14):

$$EUR_{BOE} = (a_{151}L_{hw}^2 + a_{152}L_{hw} + a_{153})NL + (a_{154}L_{hw} + a_{155})L_{hw} + a_{156} \quad (15)$$

In the equation, $EUR_{BOE}$ denotes the recoverable oil equivalent recovery ratio, %; $L_{hw}$ denotes the well distance between heating wells, m; NL denotes the number of well distance of heating wells layers, layers; $a_{151}$, $a_{152}$, $a_{153}$, $a_{154}$, $a_{155}$, $a_{156}$ denote empirical coefficients, which may be 0.0025, −0.0860, 0.8458, −0.0208, 0.7138, 93.0192, respectively.

II. Secondly, the steps of optimizing key parameters according to the above pre-established models are introduced.

1. Firstly, the above step 101 is described.

In a specific implementation, the lower limit temperature required for completely converting the convertible organic matter in the shale to be measured into oil and gas can be obtained by inputting the temperature rise rate into the pre-established relationship between the temperature rise rate and the lower limit temperature required for completely converting the convertible organic matter in the shale into oil and gas (the above equation (1)).

When the established model (equation (1)) is applied to predict the key parameters of any one research region, a "temperature rise rate" is set according to the heater, and then the "temperature rise rate" is input into the model for predicting a lower limit temperature, to obtain the lower limit temperature corresponding to the "temperature rise rate".

2. Secondly, the above step 102 is described.

In a specific implementation, according to the above equations (2) to (6), the thermal field parameters of the target reservoir of interest; the thermal field parameters of the target reservoir of interest, and the optimal heating time (the heating time corresponding to the lower limit temperature required for completely converting the convertible organic matter in the shale into oil and gas) are input into the pre-established relationship between the optimal well distance of heating wells and the optimal heating time (the above equation (7)), to determine the optimal well distance of heating wells.

3. Next, the above step 103 is described.

In a specific implementation, the oil yield equivalent of a production well in the target reservoir of interest is determined by inputting the temperature rise rate into the pre-established relationship between temperature and the oil yield equivalent of shale (the above equation (8)).

In an embodiment, the method for predicting an optimal exploitation approach for shale oil in-situ conversion further comprises: realizing prediction of the oil and gas yield ratio based on the model for predicting a ratio of oil and gas yield (the above equations (9) and (10)), i.e., inputting the temperature rise rate into the above equations (9) and (10) to obtain the oil and gas yield ratio.

4. Next, the above step 104 is described.

In a specific implementation, the method of determining an effective heating region of a peripheral heating well based on the lower limit temperature comprises: determining a region of the heating regions in which the lowest temperature reaches or exceeds the lower limit temperature required for completely converting the convertible organic matter into oil and gas, as an effective heating region.

Based on the heating well pattern, after a temperature at the center of the connection line between the heating wells reaches the lower limit temperature required for completely converting the convertible organic matter into oil and gas, according to the principle that monthly oil yield equivalent value of the production well is equal to the value of heater input energy of that month, the heating stop time of the heater is determined, and the optimal well pattern is determined based on the effective thermal field boundary of the peripheral heating well.

Based on the in-situ conversion well pattern of shale oil, preferably a triangular well pattern spacing mode is adopted (the triangular well pattern has uniform heating and high utilization rate of thermal efficiency), when the temperature at center of the connection line between the heating wells reaches the lower limit temperature required for completely converting the convertible organic matter into oil and gas, the convertible organic matter in the effective heating region controlled by the heating well is completely converted into oil and gas and is produced. The oil and gas produced by continuous heating mainly comes from the oil and gas produced by gas expansion in the effective heating region and the extension of the effective heating region in the peripheral heating well. The amount of oil and gas in this part is relatively small, and the utilization rate of thermal energy for continuing heating is relatively low, and preferably the heating is stopped when the temperature at center of the connection line between the heating wells reaches the lower limit temperature required for completely converting the convertible organic matter into oil and gas. The effective heating region refers to a region of the heating regions in which the lowest temperature reaches or exceeds the lower limit temperature required for completely converting the convertible organic matter into oil and gas.

The optimal well pattern of the heating well is determined according to the thermal field simulation to ensure the maximum efficiency of the input heat and the maximum utilization of the resources.

In an embodiment, determining an optimal well pattern based on a boundary of the effective heating region of the peripheral heating well may include:

when a vertical well pattern is adopted for the heating wells, boundaries of effective heating regions or the outermost boundaries of effective heating regions outside peripheral heating wells for adjacent development well groups overlap, and a distance between outer boundaries of effective heating regions outside peripheral heating wells of exploitation units is from 0.5 m to 5 m, and preferably 2 m;

when a horizontal well pattern is adopted for the heating wells, in a lateral direction, outer boundaries of effective heating regions or the outermost boundaries of effective heating regions outside respective peripheral heating wells for adjacent development well groups overlap, and a distance between outer boundaries of effective heating regions outside respective peripheral heating wells for adjacent exploitation units is from 0.5 m to 5 m, and preferably 2 m.

Figure 15:
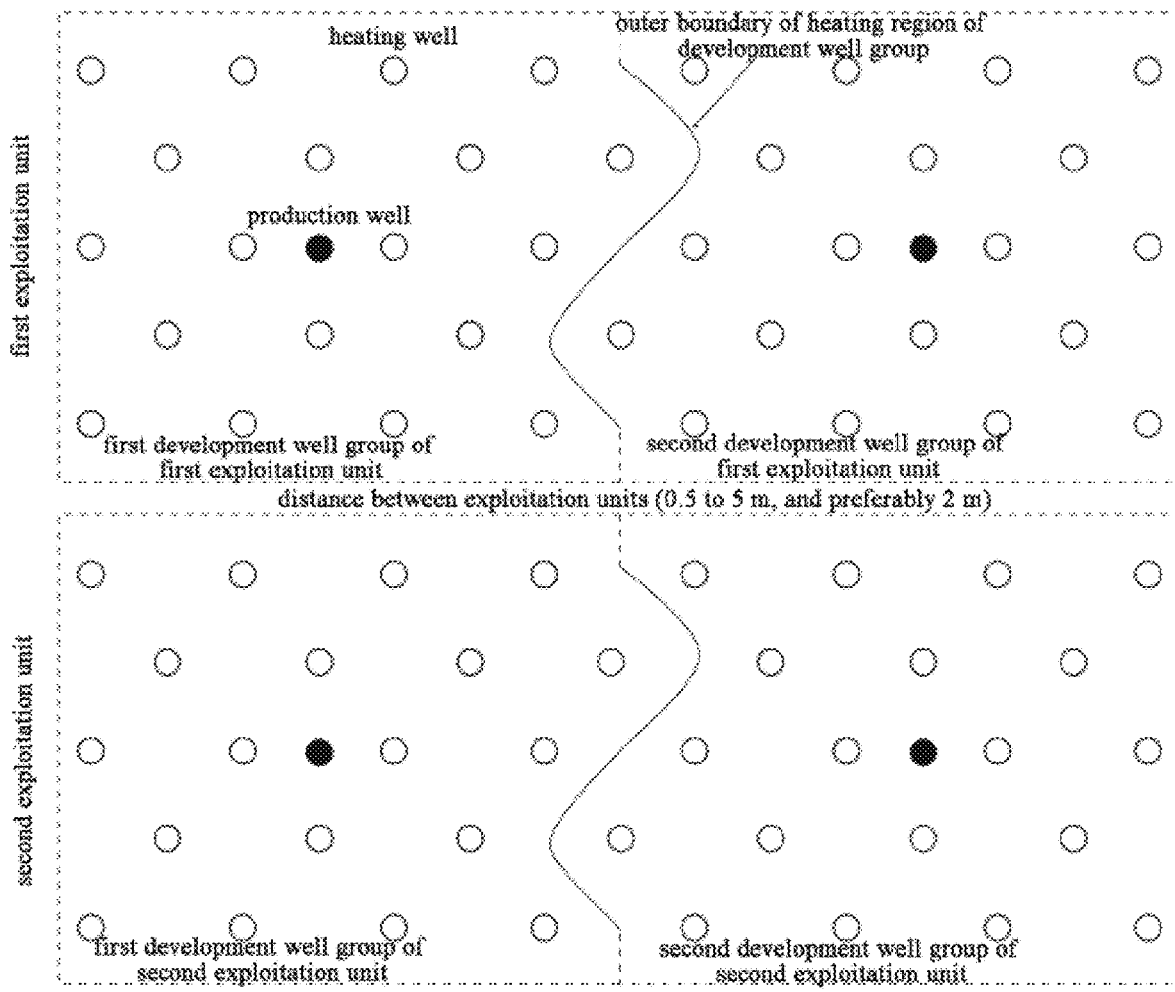
FIG. 15 is a plan view of an optimal well pattern of a vertical well pattern according to an embodiment of the present disclosure.

In a specific implementation, when a vertical well pattern is adopted for the heating wells, the peripheral heating well refers to the outermost heating well of one exploitation well group, preferably the boundaries of the effective heating regions or the outermost boundaries of the effective heating regions outside the respective adjacent peripheral heating wells of the adjacent development well groups overlap (FIG. 15). The development well group refers to well pattern units with the same well pattern and the same ratio of production wells and heating wells, and that may be duplicated. Multiple exploitation well groups can constitute one exploitation unit, and the exploitation unit refers to a group of multiple exploitation wells having the same or similar heating start time and heating end time. The outer boundaries of the effective heating regions outside the respective adjacent peripheral heating wells of the adjacent exploitation units are spaced by 0.5 to 5 m, and preferably 2 m, to ensure that the heating start time and the heating end time of adjacent exploitation units are not consistent, i.e., the production periods are not consistent, resulting in reduction of oil and gas recovery rate due to oil and gas streaming between the adjacent exploitation units.

Figure 16:
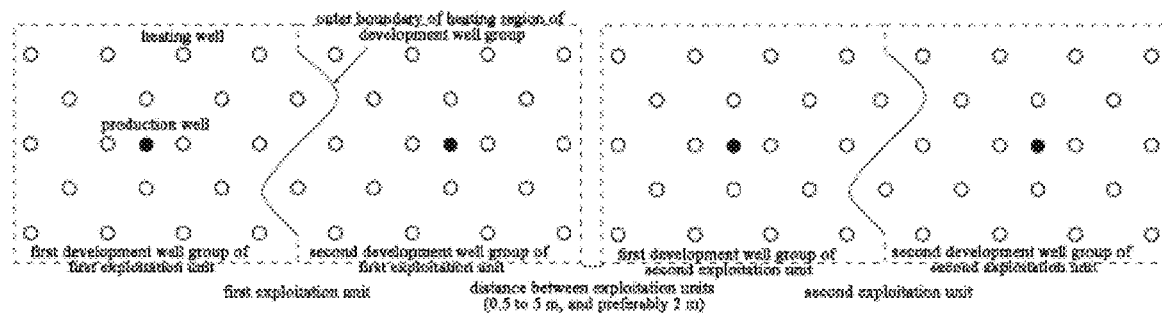
FIG. 16 is a cross-sectional view of an optimal well pattern of a horizontal well pattern according to an embodiment of the present disclosure.

In a specific implementation, when a horizontal well pattern is adopted for the heating wells, the peripheral heat wells refer to the uppermost and lowermost heating wells on the vertical profile of the heating wells, preferably the effective heating region boundary above the uppermost peripheral heating well is consistent with the upper boundary of the effective shale, and the effective heating region boundary below the lowermost peripheral heating well is consistent with the lower boundary of the effective shale (FIG. 16). In a horizontal direction, the outer boundaries of the effective heating regions or the outermost boundaries of the effective heating regions outside the respective adjacent peripheral heating wells of the adjacent development well groups overlap, the outer boundaries of the effective heating regions outside the respective adjacent peripheral heating wells of the adjacent exploitation units are spaced by 0.5 to 5 m, and preferably 2 m.

5. Next, a step of optimizing parameters after the above described step 105 is described.

In a specific implementation, the relationship between the cumulative input energy of the heater and the heating time is pre-established by performing thermal simulation experiments on a plurality of different shale samples in accordance with an in-situ conversion exploitation condition, so as to solve the problem of optimizing the input energy in the process in-situ conversion. Therefore, based on the relationship between the cumulative input energy of the heater and the heating time (the model for predicting heater cumulative input energy, for example, equation (12) above), an optimal parameter, i.e., the heater cumulative input energy, can be obtained.

In a specific implementation, the time when the temperature at center of the connection line between the heating wells reaches the lower limit temperature required for completely converting the convertible organic matter into oil and gas is the heating stop time of the heater. However, the temperature at the midpoint of the heating well line cannot be measured in actual production (unless there is an observation well), so that the heating stop time of the heater can be determined also according to the principle that monthly oil yield equivalent value of the production well is equal to the value of heater input energy of that month.

In a specific implementation, the method for obtaining the heating stop time of the heater may be such that the oil yield equivalent is obtained according to the equation (8), equal to the equation (12), according to which the "t" in the equation (12) is obtain, and the "t" is the heating stop time of the heater.

6. Next, following the above described step 105, the step of improving utilization rate of recoverable oil and gas resources to the maximum extent on the basis of ensuring the optimal exploitation approach for shale oil in-situ conversion will be described.

In an embodiment, the above described method for predicting an optimal exploitation approach for shale oil in-situ conversion may further comprise:

determining a completely converted volume ratio of the convertible organic matter in the development well group of the target reservoir of interest, based on the well distance of heating wells and a pre-established relationship between the well distance of heating wells and the completely converted volume ratio of the convertible organic matter in the development well group; wherein the completely converted volume ratio of the convertible organic matter in the development well group refers to a ratio of a volume of the convertible organic matter that totally becomes to oil and gas within a plane projection area of the effective heating region to a volume of the effective shale within the plane projection area of the effective heating region, when a temperature at a center of a connection line between the heating wells reaches the lower limit temperature within one in-situ conversion exploitation well group;

determining a recovery ratio of the recoverable oil equivalent within one development well group with the optimal well pattern when the temperature at the center of the connection line between the heating wells reaches the lower limit temperature, based on the well distance between heating wells, the number of layers in the well pattern of the target reservoir of interest, and a pre-established relationship between the well distance between heating wells, the number of layers in the well pattern and a recovery ratio of the recoverable oil equivalent within the development well group; wherein the relationship between the well distance between heating wells, the number of layers in the well pattern and the recovery ratio of the recoverable oil equivalent within the development well group is pre-established by performing thermal simulation experiments on a plurality of different shale samples in accordance with an in-situ conversion exploitation condition.

Figure 17:
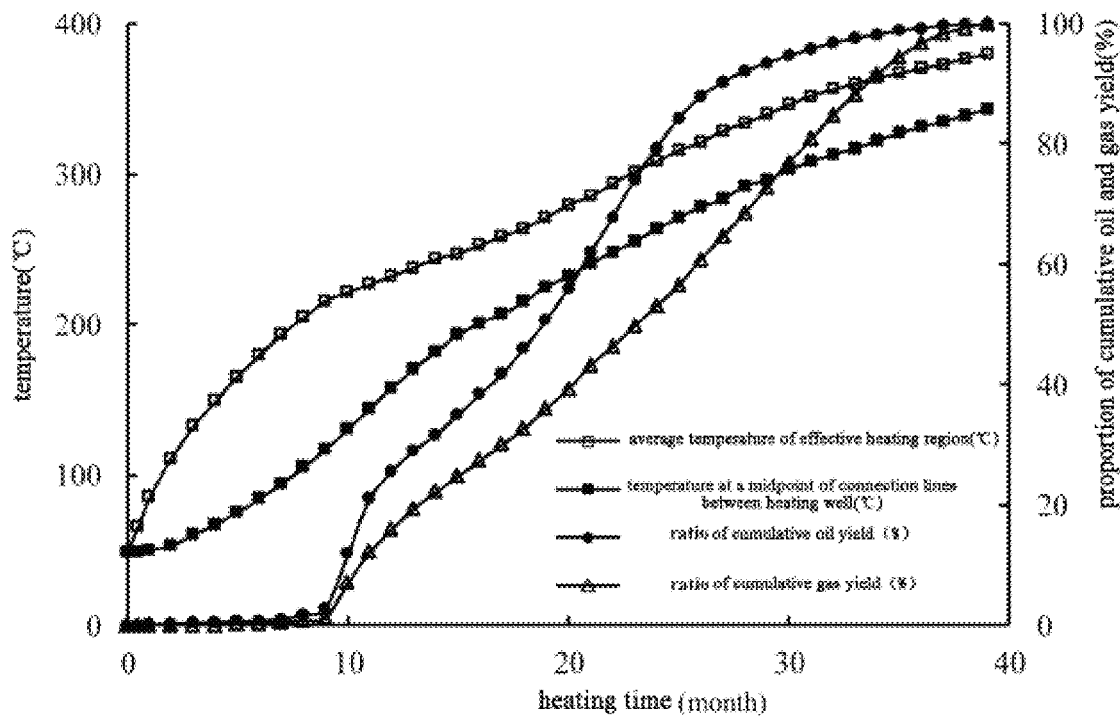
FIG. 17 is a diagram showing a relationship between a simulated heating time, a temperature, a ratio of cumulative oil yield and a ratio of gas yield in shale in-situ conversion according to an embodiment of the present disclosure.

In the example of the disclosure, shale from 7 long sections of the Ordos Basin is selected, the TOC is 22.4%, the Ro is 0.81%, and the effective shale has a continuous thickness of 16.6 m. In heating well horizontal spacing of three layers, in the condition that the well distance of heating wells is 6.5 meters, the temperature at center of the connection line between the heating wells reaches 331° C., that is the lower limit temperature for completely converting the convertible organic matter. A diagram is obtained showing a relationship between the average temperature of the effective heating region, the temperature at center of the connection line between the heating wells, the cumulative oil yield ratio and the cumulative gas yield ratio with the heating time (FIG. 17).

Figure 18:
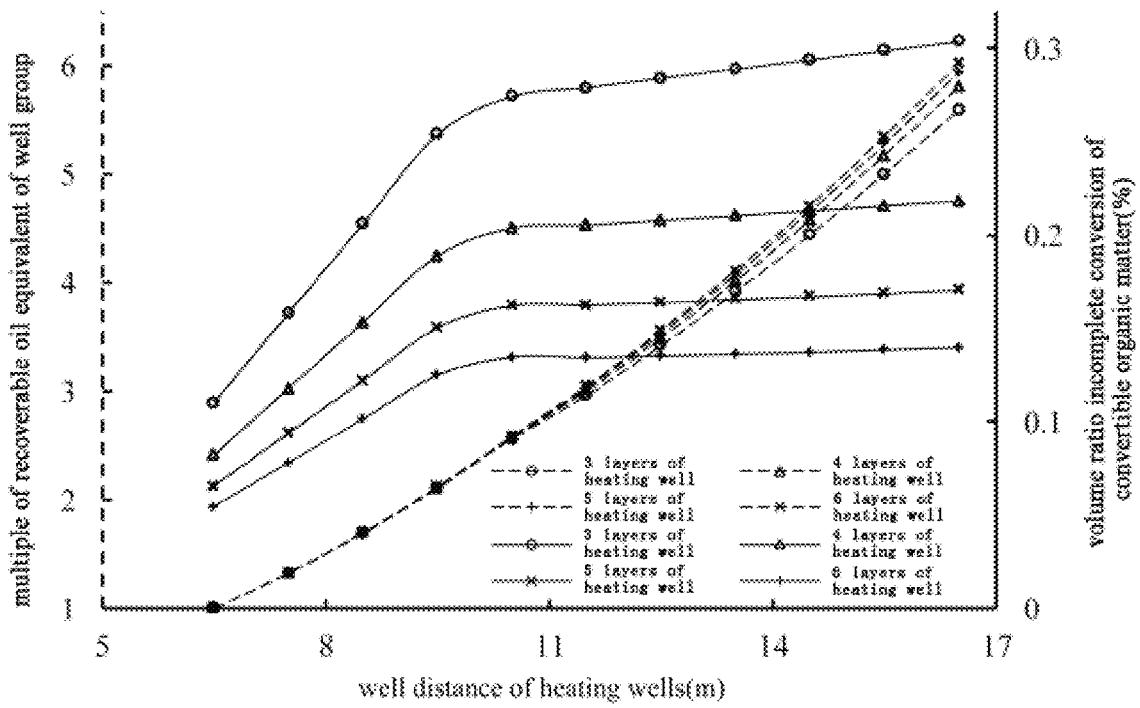
FIG. 18 is a diagram showing a relationship between a well distance of heating wells within a group of exploitation wells for shale in-situ conversion, a recoverable oil equivalent multiple and an incompletely converted volume ratio of convertible organic matter according to an embodiment of the present disclosure.

In the optimal well pattern of the horizontal heating wells, difference occurs in different well distances between heating wells, different effective shale thickness (different numbers of heating well layers), the recoverable oil equivalent controlled within one development well group, and the completely converted volume ratio of the convertible organic matter in the development well group, the recoverable oil equivalent controlled in the optimal well pattern (FIG. 12) of the horizontal heating well having the well distance of heating wells of 6.5 m is taken as a base value, which is set to be 1, and difference occurs in a recoverable oil equivalent multiple and the completely converted volume ratio of the convertible organic matter in the development well group controlled within one development well group having different well distances between heating wells and different numbers of heating layers. In the case that other conditions are the same, the recoverable oil equivalent multiple of the well group increases with the increase of the well distance of heating wells and increases with the increase of the number of heating layers; the completely converted volume ratio of the convertible organic matter in the development well group increases with the increase of the well distance of heating wells and decreases with the increase of the number of heating layers (FIG. 18).

Based on the same inventive concept, the embodiment of the present disclosure further provides an apparatus for predicting an optimal exploitation approach for shale oil in-situ conversion, as described in the following embodiment. Since the principle based on which the apparatus for predicting an optimal exploitation approach for shale oil in-situ conversion solves problems is similar to the method for predicting an optimal exploitation approach for shale oil in-situ conversion, the implementation of the apparatus for predicting an optimal exploitation approach for shale oil in-situ conversion can be seen by referring to the implementation of the method for predicting an optimal exploitation approach for shale oil in-situ conversion, and repetition will not be described in detail. As used below, the term "unit" or "module" can realize combination of software and/or hardware with predetermined functions. Although preferably the apparatus described in the following embodiment is implemented by software, implementation by hardware, or combination of software and hardware is also possible and is conceivable.

Figure 19:
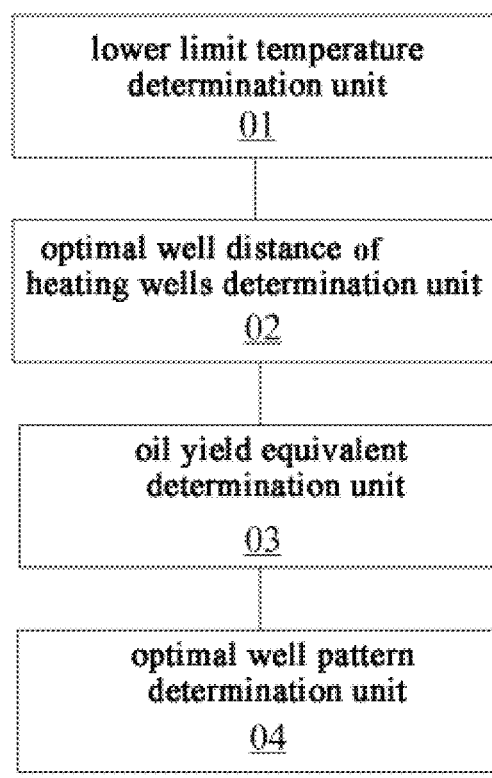
FIG. 19 is a structural schematic of an apparatus for predicting an optimal exploitation approach for shale oil in-situ conversion according to an embodiment of the present disclosure.

FIG. 19 is a structural schematic of an apparatus for predicting an optimal exploitation approach for shale oil in-situ conversion according to an embodiment of the present disclosure. The apparatus comprises:

a lower limit temperature determination unit 01 for determining a lower limit temperature required for completely converting convertible organic matter in a shale to be measured into oil and gas based on a temperature rise rate and a pre-established relationship between the temperature rise rate and the lower limit temperature required for completely converting the convertible organic matter in the shale into oil and gas;

an optimal well distance of heating wells determination unit 02 for determining an optimal well distance of heating wells, based on a thermal field parameter of a target reservoir of interest, an optimal heating time corresponding to the lower limit temperature, and a pre-established relationship between an optimal well distance of heating wells and the optimal heating time;

an oil yield equivalent determination unit 03 for determining an oil yield equivalent of a production well in the target reservoir of interest, based on the temperature rise rate and a pre-established relationship between a temperature and an oil yield equivalent of the shale;

an optimal well pattern determination unit 04 for determining an effective heating region of a peripheral heating well based on the lower limit temperature and determining an optimal well pattern, based on a boundary of the effective heating region of the peripheral heating well;

wherein the relationship between the temperature rise rate and the lower limit temperature required for completely converting the convertible organic matter in the shale into oil and gas, the relationship between the well distance of heating wells and the optimal heating time, and the relationship between the temperature and the oil yield equivalent of the shale are pre-established by performing thermal simulation experiments on a plurality of different shale samples in accordance with an in-situ conversion exploitation condition; and the lower limit temperature, the optimal well distance of heating wells, the oil yield equivalent and the optimal well pattern are optimal parameters in the optimal exploitation approach for shale oil in-situ conversion.

In an embodiment, the optimal well pattern determination unit is specifically used for:

when a vertical well pattern is adopted for the heating wells, boundaries of effective heating regions or the outermost boundaries of effective heating regions outside peripheral heating wells for adjacent development well groups overlap, and a distance between outer boundaries of effective heating regions outside peripheral heating wells of exploitation units is from 0.5 m to 5 m; and when a horizontal well pattern is adopted for the heating wells, in a lateral direction, outer boundaries of effective heating regions or the outermost boundaries of effective heating regions outside respective peripheral heating wells for adjacent development well groups overlap, and a distance between outer boundaries of effective heating regions outside respective peripheral heating wells for adjacent exploitation units is from 0.5 m to 5 m.

In an embodiment, the above described relationship between the temperature rise rate and the lower limit temperature required for completely converting the convertible organic matter in the shale into oil and gas is a model for predicting a lower limit temperature as described below:

$$T_{end} = a_1 \times TR^{b1};$$

wherein, $T_{end}$ denotes the lower limit temperature required for completely converting the convertible organic matter in the shale to be measured into oil and gas; TR denotes the temperature rise rate; and $a_1$, $b_1$ denote empirical coefficients.

In an embodiment, the relationship between the optimal well distance of heating wells and the optimal heating time is pre-established according to the following process:

establishing a relationship between a thermal diffusion coefficient and a temperature based on thermal diffusion coefficients at different temperature points that are measured by a laser thermal conductivity instrument in a process of a thermal simulation experiment;

establishing a relationship between a specific heat capacity and a temperature based on specific heat capacities at different temperature points that are measured by a simultaneous thermal analyzer in a process of a thermal simulation experiment;

establishing a relationship between a shale thermal conductivity and a temperature based on shale densities at different temperature points that are measured by a thermal dilatometer in a process of a thermal simulation experiment; and establishing a relationship between the optimal well distance of heating wells and the optimal heating time, by determining, through thermal field simulation, various optimal heating time with which all the effective heating regions of the shale reach the lower limit temperature under a condition of various well distances of heating wells, based on the relationship between the thermal diffusion coefficients and the temperature, the relationship between the specific heat capacity and the temperature, and the relationship between the shale thermal conductivity and the temperature.

In an embodiment, the relationship between the thermal diffusion coefficients and the temperature comprises a model for predicting a thermal diffusion coefficient in a vertical direction and a model for predicting a thermal diffusion coefficient in a horizontal direction;

the model for predicting the thermal diffusion coefficient in the vertical direction is: $\alpha_v = a_2 \ln(T) + b_2$;

wherein, $\alpha_v$ denotes the thermal diffusion coefficient in the vertical direction; T denotes temperature; and $a_2$, $b_2$ denote empirical coefficients.

the model for predicting the thermal diffusion coefficient in the horizontal direction is: $\alpha_h = a_3 e^{b_3 T}$.

wherein, $\alpha_h$ denotes the thermal diffusion coefficient in the horizontal direction; T denotes temperature; and $a_3$, $b_3$ denote empirical coefficients.

The relationship between the specific heat capacity and the temperature comprises a model for predicting a specific heat capacity in a vertical direction and a model for predicting a specific heat capacity in a horizontal direction.

The model for predicting the specific heat capacity in the vertical direction is: $Cp_v = a_{41}T^3 + a_{42}T^2 + a_{43}T + b_4$;

wherein, $Cp_v$ denotes the specific heat capacity in the vertical direction; T denotes temperature; and $a_{41}$, $a_{42}$, $a_{43}$, $b_4$ denote empirical coefficients.

The model for predicting the specific heat capacity in the horizontal direction is: $Cp_h = a_5 \ln(T) + b_5$;

wherein, $Cp_h$ denotes the specific heat capacity in the horizontal direction; T denotes temperature; and $a_5$, $b_5$ denote empirical coefficients.

The relationship between the shale thermal conductivity and the temperature is a model for predicting a shale thermal conductivity as described below:

$$\lambda = \alpha \times Cp \times \rho.$$

wherein, $\lambda$ denotes the thermal conductivity; T denotes the temperature; $\alpha$ denotes the thermal diffusion coefficient; Cp denotes the specific heat capacity; and $\rho$ denotes a shale density.

In an embodiment, the relationship between the optimal well distance of heating wells and the optimal heating time is a model for predicting an optimal well distance of heating wells as described below:

$$t_{Oh} = f(\lambda) \begin{cases} a_{71}L_{hw} + b_{71} & L_{hw} < 8m \\ a_{72}L_{hw}^3 + a_{73}L_{hw}^2 + a_{74}L_{hw} + b_{72} & L_{hw} \geq 8m \end{cases};$$

wherein, $t_{oh}$ denotes the optimal heating time of the heating well, $L_{hw}$ denotes the optimal well distance of heating wells, $f(\lambda)$ denotes a ratio of a measured value of the thermal conductivity of shale sample to be measured to a calculated value thereof, $a_{71}$, $b_{71}$, $a_{72}$, $a_{73}$, $a_{74}$, $b_{72}$ denote empirical coefficients; and the calculated value is determined according to the thermal diffusion coefficient and the specific heat capacity.

In an embodiment, the relationship between the temperature and the oil yield equivalent of shale is a model for predicting an oil yield equivalent as described below:

$$RQ_{BOE} = \Delta T \times ((a_8 ST + b_8)ST + c_8) + RQ_{50}$$

wherein, $\Delta T = |T - T_{50}|$; $ST = \operatorname{Sin}(\ln(\Delta T))$;

$RQ_{BOE}$ denotes a ratio of a cumulative oil yield equivalent corresponding to a temperature to a total cumulative oil yield equivalent; T denotes a temperature corresponding to a preset cumulative oil yield equivalent; $T_{50}$ denotes a temperature corresponding to 50% of the total cumulative oil yield equivalent, in unit of ° C.; $RQ_{50}$ denotes a ratio of a cumulative oil yield equivalent corresponding to the temperature $T_{50}$; and $a_8$, $b_8$, $c_8$ denote empirical coefficients.

In an embodiment, the method further comprises: pre-establishing a model for predicting a ratio of oil and gas yield as described below by performing thermal simulation experiments on a plurality of different shale samples in accordance with an in-situ conversion exploitation condition:

$$RQ_{gas} = a_9 \ln(TR) + b_9;$$

$$RQ_{oil} = a_{10}TR^{b_{10}};$$

wherein, $RQ_{gas}$ denotes a ratio of produced hydrocarbon gas to the hydrocarbon gas produced by an aluminum thermal simulation method (FA); $RQ_{oil}$ denotes a ratio of oil yield to the oil yield produced by the aluminum thermal simulation method (FA); TR denotes the temperature rise rate; and $a_9$, $b_9$, $b_{10}$, $b_{10}$ denote empirical coefficients.

In an embodiment, the apparatus for predicting an optimal exploitation approach for shale oil in-situ conversion further comprises: an establishment unit of a relationship between cumulative input energy of a heater and heating time, for pre-establishing a relationship between cumulative input energy of a heater and heating time; the relationship between the cumulative input energy of the heater and the heating time is a model for predicting heater cumulative input energy as described below:

$$E_{cum} = \sum_{i=1}^{n}\sum_{j=1}^{m} E_{instant\_ij};$$

wherein, $E_{cum}$ denotes the cumulative input energy of the heater in the nth month, $E_{instant\_ij}$ denotes instantaneous input energy of the heater on the jth day in the ith month; n denotes cumulative heating time of the heater; m denotes the number of days of the ith month;

$E_{instant\_ij}$ is calculated according to a model for predicting heater instantaneous input energy as described below:

$$E_{instant} = \begin{cases} a_{111}e^{b_{111}t} & t < 6 \\ a_{112}\ln(t) + b_{112} & t \geq 6 \end{cases};$$

$E_{instant}$ denotes instantaneous input energy required at the corresponding heating time t of the heater; t denotes the heating time; and $a_{111}$, $b_{111}$, $a_{112}$, $b_{112}$ denote empirical coefficients.

In an embodiment, the above described apparatus for predicting an optimal exploitation approach for shale oil in-situ conversion may further comprise:

a completely converted volume ratio determination unit for determining a completely converted volume ratio of the convertible organic matter in the development well group of the target reservoir of interest, based on the well distance of heating wells and a pre-established relationship between the well distance of heating wells and the completely converted volume ratio of the convertible organic matter in the development well group; wherein the completely converted volume ratio of the convertible organic matter in the development well group refers to a ratio of a volume of the convertible organic matter that totally becomes to oil and gas within a plane projection area of the effective heating region to a volume of the effective shale within the plane projection area of the effective heating region, when a temperature at a center of a connection line between the heating wells reaches the lower limit temperature within one in-situ conversion exploitation well group;

a recovery ratio of recoverable oil equivalent determination unit for determining a recovery ratio of the recoverable oil equivalent within one development well group with the optimal well pattern when the temperature at the center of the connection line between the heating wells reaches the lower limit temperature, based on the well distance between heating wells, the number of layers in the well pattern of the target reservoir of interest, and a pre-established relationship between the well distance between heating wells, the number of layers in the well pattern and a recovery ratio of the recoverable oil equivalent within the development well group; wherein the relationship between the well distance between heating wells, the number of layers in the well pattern and the recovery ratio of the recoverable oil equivalent within the development well group is pre-established by performing thermal simulation experiments on a plurality of different shale samples in accordance with an in-situ conversion exploitation condition.

In an embodiment, the relationship between the well distance of heating wells and the completely converted volume ratio of the convertible organic matter in the development well group is a model for predicting completely converted volume ratio of convertible organic matter in a development well group as described below:

$$RUV = 100 - \begin{cases} a_{131}L_{hw}^{b_{131}} + c_{131}\ln(L_{hw}) + d_1 & L_{hw} \leq 10m \\ a_{132}L_{hw}^{b_{132}} + c_{132}L_{hw} & L_{hw} > 10m \end{cases};$$

wherein, RUV denotes the completely converted volume ratio of the convertible organic matter in the development well group; $L_{hw}$ denotes the well distance between heating wells; and $a_{131}$, $b_{131}$, $c_{131}$, $d_{131}$, $a_{132}$, $b_{132}$, $c_{132}$ denote empirical coefficients.

In an embodiment, the relationship between the well distance between heating wells, the number of layers in the well pattern and the recovery ratio of the recoverable oil equivalent within the development well group is a model for predicting a recovery ratio of recoverable oil equivalent as described below:

$$EUR_{BOE} = (a_{151}L_{hw}^2 + a_{152}L_{hw} + a_{153})NL + (a_{154}L_{hw} + a_{155})L_{hw} + a_{156};$$

wherein, $EUR_{BOE}$ denotes the recovery ratio of the recoverable oil equivalent; $L_{hw}$ denotes the well distance between heating wells; NL denotes the number of layers in the well pattern of the heating wells; and $a_{151}$, $a_{152}$, $a_{153}$, $a_{154}$, $a_{155}$, $a_{156}$, denote empirical coefficients.

There is further provided in embodiments of the present disclosure a computer device comprising a memory, a processor, and a computer program stored on the memory and executable by the processor, wherein the processor, when executing the computer program, implements the method for predicting an optimal exploitation approach for shale oil in-situ conversion as described above.

There is further provided in embodiments of the present disclosure a computer readable storage medium storing therein a computer program for performing the method for predicting an optimal exploitation approach for shale oil in-situ conversion as described above.

The technical solution provided in the embodiments of the present disclosure achieves the following advantageous technical effects.

Firstly, the relationship between the temperature rise rate and the lower limit temperature required for completely converting the convertible organic matter in the shale into oil and gas, and the relationship between the optimal well distance of heating wells and the optimal heating time are pre-established by performing thermal simulation experiments on a plurality of different shale samples based on an in-situ conversion exploitation condition, so as to solve the problem in the prior art that the lower limit temperature and the optimal well distance of heating wells in the well patterns of different well distances between heating wells. Therefore, based on the relationship between the temperature rise rate and the lower limit temperature as well as the relationship between the optimal well distance of heating wells and the optimal heating time, the optimal parameters, i.e., the lower limit temperature and the optimal well distance of heating wells, can be obtained.

Secondly, the relationship between the temperature and the oil yield equivalent of shale is pre-established by performing thermal simulation experiments on a plurality of different shale samples in accordance with an in-situ conversion exploitation condition, so as to solve the technical problem that the oil and gas yield cannot be optimized in in-situ conversion process due to different temperatures in different regions. Therefore, an optimal parameter, i.e., an oil yield equivalent, can be obtained based on the relationship between temperature and the oil yield equivalent of shale.

In addition, the optimal well pattern is determined based on a boundary of the effective heating region of the peripheral heating well, thereby obtaining an optimal parameter, i.e., an optimal well pattern.

In summary, the technical solution provided in the embodiments of the present disclosure determines an optimal exploitation approach for shale oil in-situ conversion based on optimal parameters obtained by optimizing key parameters during shale oil in-situ conversion and exploitation, thereby reducing the exploitation cost and providing a scientific guidance for shale oil in-situ conversion exploitation.

Persons skilled in the art shall understand that, the embodiments of the present disclosure can be provided as a method, a system or a computer program product. Therefore, the present disclosure can adopt the forms of a full hardware example, a full software example, or combination of a software example and a hardware example. Moreover, the present disclosure can adopt the form of a computer program product that is implemented on one or more computer-usable storage medium (comprising but not limited to a disk memory, a CD-ROM, an optical memory, etc.) comprising computer-usable program codes.

The disclosure is described with reference to flow diagrams and/or block diagrams of the method, the device (system) and the computer program product according to the embodiment of the disclosure. It should be understood that each flow and/or block in the flow diagrams and/or block diagrams, and the combination of the flows and/or blocks in the flow diagrams and/or block diagrams can be achieved by computer program commands. These computer program commands can be provided to a CPU of a general-purpose computer, a special-purpose computer, an embedded processor or other programmable data processing device to produce a machine, so that a device for achieving functions designated in one or more flows in the flow diagrams and/or one or more blocks in the block diagrams can be generated by the command executed by the CPU of the computer or other programmable data processing device.

These computer program commands can also be stored in a computer-readable memory that can guide a computer or other programmable data processing device to operate in a special way, so that the command stored in the computer-readable memory generates a manufactured product comprising a command device which achieves functions designated in one or more flows in the flow diagrams and/or one or more blocks in the block diagrams.

These computer program commands can also be loaded on a computer or other programmable data processing device, on which a series of operation steps are executed to generate processing achieved by the computer, so that the command executed on the computer or other programmable data processing device is provided for being used in the steps of achieving functions designated in one or more flows in the flow diagrams and/or one or more blocks in the block diagrams.

The foregoing is merely a preferred embodiment of the present disclosure and is not intended to limit the present disclosure, and various modifications and variations can be made to the embodiment of the present disclosure by those skilled in the art. Any modifications, equivalents, improvements, etc. made within the spirit and principle of the present disclosure are intended to be included within the protection scope of the present disclosure.

What is claimed is:

1. A method for predicting an optimal exploitation approach for shale oil in-situ conversion; comprising:
   a) collecting a plurality of shale samples in a target reservoir of interest and performing a plurality of thermal simulation experiments on the plurality of shale samples according to an in-situ conversion exploitation condition to pre-establish a relationship between a temperature rise rate and a lower limit temperature required for completely converting convertible organic matter in shale into oil and gas, a relationship between a well distance of heating wells and a heating time, and a relationship between a temperature and an oil field equivalent of the shale, and to obtain a plurality of thermal field parameters varying with the temperature;
      wherein the plurality of thermal field parameters comprise a thermal diffusion coefficient a specific the at capacity and a thermal conductivity;
      wherein in the plurality of thermal simulation experiments, the thermal diffusion coefficient, the specific heat capacity, and the thermal conductivity are measured by using a laser thermal conductivity instrument, a simultaneous thermal analyzer, and a thermal dilatometer, respectively;
   b) determining, by a processor, the lower limit temperature required for completely converting the convertible organic matter in the shale to be measured into the oil and the gas based on the temperature rise rate and the pre-established relationship between the temperature rise rate and the lower limit temperature required for completely converting the convertible organic matter in the shale into the oil and the gas;
   c) determining, by the processor, an optimal well distance of the heating wells based on the thermal field parameter of the target reservoir of interest, an optimal heating time corresponding to the lower limit temperature, and the pre-established relationship between the optimal well distance of the heating wells and the optimal heating time;
   d) determining, by the processor, an oil yield equivalent of a production well in the target reservoir of interest, based on the temperature rise rate and the pre-established relationship between the temperature and the oil yield equivalent of the shale;
   e) determining, by the processor, an effective heating region of a peripheral heating well based on the lower limit temperature; and
   f) determining by the processor, an optimal well pattern based on a boundary of the effective heating region of the peripheral heating well;
      wherein the lower limit temperature, the optimal well distance of the heating wells, the oil yield equivalent, and the optimal well pattern are optimal parameters in the optimal exploitation approach for the shale oil in-situ conversion; and
      wherein the completely converting of convertible organic matter in the shale into the oil and the gas refers to a converted volume ratio of the convertible organic matter being 100%.

2. The method according to claim 1, wherein the determining the optimal well pattern based on the boundary of the effective heating region of the peripheral heating well comprises:

wherein when a vertical well pattern is adopted for the heating wells, boundaries of effective heating regions or outermost boundaries of the effective heating regions outside peripheral heating wells for adjacent development well groups overlap, and a distance between outer boundaries of the effective heating regions outside the peripheral heating wells of exploitation units is from 0.5 m to 5 m; and wherein when a horizontal well pattern is adopted for the heating wells, in a lateral direction, the outer boundaries of the effective heating regions or the outermost boundaries of the effective heating regions outside respective peripheral heating wells for the adjacent development well groups overlap, and the distance between the outer boundaries of the effective heating regions outside the respective peripheral heating wells for adjacent exploitation units is from 0.5 m to 5 m.

3. The method according to claim 1, wherein the relationship between the temperature rise rate and the lower limit temperature required for completely converting the convertible organic matter in the shale into the oil and the gas is a model for predicting the lower limit temperature as described below:

$$T_{end} = a_1 \times TR^{b_1};$$

wherein $T_{end}$ denotes the lower limit temperature required for completely converting the convertible organic matter in the shale to be measured into the oil and the gas, TR denotes the temperature rise rate, and $a_1$ and $b_1$ denote empirical coefficients.

4. The method according to claim 1, wherein the relationship between the optimal well distance of the heating wells and the optimal heating time is pre-established according to the following process:

i) establishing a relationship between the thermal diffusion coefficient and the temperature based on thermal diffusion coefficients at different temperature points that are measured by the laser thermal conductivity instrument in the plurality of thermal simulation experiments;

ii) establishing a relationship between the specific heat capacity and the temperature based on specific heat capacities at different temperature points that are measured by the simultaneous thermal analyzer in the thermal simulation experiment;

iii) establishing a relationship between a shale thermal conductivity and the temperature based on shale densities at different temperature points that are measured by the thermal dilatometer in the thermal simulation experiment; and iv) establishing the relationship between the optimal well distance of the heating wells and the optimal heating time, by determining, through thermal field simulation, various optimal heating times with which all effective heating regions of the shale reach the lower limit temperature under various well distances of the heating wells; based on the relationship between the thermal diffusion coefficients and the temperature, the relationship between the specific heat capacity and the temperature, and the relationship between the shale thermal conductivity and the temperature.

5. The method according to claim 4, wherein the relationship between the thermal diffusion coefficient and the temperature comprises a model for predicting the thermal diffusion coefficient in a vertical direction and a model for predicting the thermal diffusion coefficient in a horizontal direction;

wherein the model for predicting the thermal diffusion coefficient in the vertical direction is: $\alpha_v = a_2 \ln(T) + b_2$;

wherein; $\alpha_v$ denotes the thermal diffusion coefficient in the vertical direction, T denotes the temperature, and $a_2$ and $b_2$ denote empirical coefficients;

wherein the model for predicting the thermal diffusion coefficient in the horizontal direction is: $\alpha_h = a_3 e^{b_3 T}$;

wherein $\alpha_h$ denotes the thermal diffusion coefficient in the horizontal direction, T denotes the temperature, and $a_3$ and $b_3$ denote empirical coefficients;

wherein the relationship between the specific heat capacity and the temperature comprises a model for predicting the specific heat capacity in the vertical direction and a model for predicting the specific heat capacity in the horizontal direction;

wherein the model for predicting the specific heat capacity in the vertical direction is: $Cp_v = a_{41} T^3 + a_{42} T^2 + a_{43} T + b_4$;

wherein $Cp_v$ denotes the specific heat capacity in the vertical direction; T denotes the temperature; and $a_{41}$, $a_{42}$, $a_{43}$, and $b_4$ denote empirical coefficients;

wherein the model for predicting the specific heat capacity in the horizontal direction is: $Cp_h = a_5 \ln(T) + b_5$;

wherein $Cp_h$ denotes the specific heat capacity in the horizontal direction, T denotes the temperature, and $a_5$ and $b_5$ denote empirical coefficients;

wherein the relationship between the shale thermal conductivity and the temperature is a model for predicting the shale thermal conductivity as described below:

$$\lambda = \alpha \times Cp \times \rho;$$

wherein, $\lambda$ denotes the thermal conductivity, T denotes the temperature, $\alpha$ denotes the thermal diffusion coefficient, Cp denotes the specific heat capacity, and $\rho$ denotes a shale density.

6. The method according to claim 1, wherein the relationship between the optimal well distance of the heating wells and the optimal heating time is a model for predicting the optimal well distance of the heating wells as described below:

$$t_{oh} = f(\lambda) \begin{cases} a_{71} L_{hw} + b_{71} & L_{hw} < 8m \\ a_{72} L_{hw}^3 + a_{73} L_{hw}^2 + a_{74} L_{hw} + b_{72} & L_{hw} \geq 8m \end{cases};$$

wherein; $t_{oh}$ denotes the optimal heating time of the heating well; $L_{hw}$ denotes the optimal well distance of the heating wells; $f(\lambda)$ denotes a ratio of a measured value of the thermal conductivity of the shale sample to be measured to a calculated value; and $a_{71}$, $b_{71}$, $a_{72}$, $a_{73}$, $a_{74}$, and $b_{72}$ denote empirical coefficients; and wherein the calculated value is determined from the thermal diffusion coefficient and the specific heat capacity.

7. The method according to claim 1, wherein the relationship between the temperature and the oil yield equivalent of the shale is a model for predicting the oil yield equivalent as described below:

$$RQ_{BOE} = \Delta T \times ((a_8 ST + b_8) ST + c_8) + RQ_{50};$$

wherein; $\Delta T=|T-T_{50}|$;

wherein $ST=\operatorname{Sin}(\ln(\Delta T))$; and wherein $RQ_{BOE}$ denotes a ratio of a cumulative oil yield equivalent corresponding the temperature to a total cumulative oil yield equivalent; T denotes a temperature corresponding to a preset cumulative oil yield equivalent; $T_{50}$ denotes a temperature corresponding to 50% of the total cumulative oil yield equivalent, in unit of ° C.; $RQ_{50}$ denotes a ratio of a cumulative oil yield equivalent corresponding to the temperature $T_{50}$; and $a_8$, $b_8$, and $c_8$ denote empirical coefficients.

8. The method according to claim 1, further comprising: pre-establishing a relationship between cumulative input energy of a heater and the heating time;

wherein the relationship between the cumulative input energy of the heater and the heating time is a model for predicting the heater cumulative input energy as described below:

$$E_{cum} = \sum_{i=1}^{n} \sum_{j=1}^{m} E_{instant\_ij};$$

wherein $E_{cum}$ denotes the cumulative input energy of the heater in an nth month, $E_{instant\_ij}$ denotes instantaneous input energy of the heater on a $j^{th}$ day in an $i^{th}$ month, n denotes cumulative heating time of the heater, and m denotes the number of days of the $i^{th}$ month;

wherein $E_{instant\_ij}$ is calculated according to a model for predicting heater instantaneous input energy as described below:

$$E_{instant} = \begin{cases} a_{111}e^{b_{111}t} & t<6 \\ a_{112}\ln(t)+b_{112} & t\geq 6 \end{cases};$$

and wherein $E_{instant}$ denotes the instantaneous input energy required at a corresponding heating time t of the heater; t denotes the heating time; and $A_{111}$, $b_{111}$, $A_{112}$, and $b_{112}$ denote empirical coefficients.

9. The method according to claim 1, further comprising:

a) determining the converted volume ratio of the convertible organic matter in a development well group of the target reservoir of interest, based on the well distance of the heating wells and a pre-established relationship between the well distance of the heating wells and the converted volume ratio of the convertible organic matter in the development well group;

wherein the converted volume ratio of the convertible organic matter in the development well group refers to a ratio of a volume of the convertible organic matter that totally becomes oil and gas within a plane projection area of the effective heating region to a volume of effective shale within the plane projection area of the effective heating region when a temperature at a center of a connection line between the heating wells reaches the lower limit temperature within one in-situ conversion exploitation well group; and b) determining a recovery ratio of the recoverable oil equivalent within one development well group with the optimal well pattern when the temperature at the center of the connection line between the heating wells reaches the lower limit temperature based on the well distance of the heating wells, a number of layers in the well pattern of the target reservoir of interest, and a pre-established relationship among the well distance of the heating wells, the number of layers in the well pattern, and a recovery ratio of the recoverable oil equivalent within the development well group;

wherein the relationship among the well distance of the heating wells, the number of layers in the well pattern and the recovery ratio of the recoverable oil equivalent within the development well group is pre-established by performing the plurality of thermal simulation experiments on a plurality of different shale samples in accordance with the in-situ conversion exploitation condition.

10. The method according to claim 9, wherein the relationship between the well distance of the heating wells and the converted volume ratio of the convertible organic matter in the development well group is a model for predicting the completely converted volume ratio of the convertible organic matter in the development well group as described below:

$$RUV = 100 - \begin{cases} a_{131}L_{hw}^{b_{131}} + c_{131}\ln(L_{hw}) + d_1 & L_{hw} \leq 10m \\ a_{132}L_{hw}^{b_{132}} + c_{132}L_{hw} & L_{hw} > 10m \end{cases};$$

wherein RUV denotes the converted volume ratio of the convertible organic matter in the development well group; $L_{hw}$ denotes the well distance of the heating wells; and $a_{131}$, $b_{131}$, $c_{131}$, $d_{131}$, $a_{132}$, $b_{132}$, and $c_{132}$ denote empirical coefficients.

11. The method according to claim 9, wherein the relationship among the well distance of heating wells, the number of layers in the well pattern, and the recovery ratio of the recoverable oil equivalent within the development well group is presented as a model for predicting a recovery ratio of recoverable oil equivalent as described below:

$$EUR_{BOE}=(a_{151}L_{hw}^2+a_{152}L_{hw}+a_{153})NL+(a_{154}L_{hw}+a_{155})L_{hw}+a_{156};$$

wherein $EUR_{BOE}$ denotes the recovery ratio of the recoverable oil equivalent; $L_{hw}$ denotes the well distance of the heating wells; NL denotes the number of layers in the well pattern of the heating wells; and $a_{151}$, $a_{152}$, $a_{153}$, $a_{154}$, $a_{155}$, and $a_{156}$ denote empirical coefficients.

12. The method according to claim 1, further comprising: pre-establishing a model for predicting a ratio of oil and gas yield as described below by performing the plurality of thermal simulation experiments on a plurality of different shale samples in accordance with the in-situ conversion exploitation condition:

$$RQ_{gas}=a_9 \ln(TR)+b_9;$$

$$RQ_{oil}=a_{10}TR^{b_{10}};$$

wherein $RQ_{gas}$ denotes a ratio of produced hydrocarbon gas to the hydrocarbon gas produced by an aluminum thermal simulation method (FA), $RQ_{oil}$ denotes a ratio of oil yield to the oil yield produced by the aluminum thermal simulation method (FA), TR denotes the temperature rise rate, and $a_9$, $b_9$, $a_{10}$, and $b_{10}$ denote empirical coefficients.

13. An apparatus for predicting an optimal exploitation approach for shale oil in-situ conversion which comprises:

a memory, a processor, and a computer program stored on the memory and executable by the processor;

wherein the processor implements, when executing the computer program, the acts of:
a) determining a lower limit temperature required for completely converting convertible organic matter in a shale to be measured into oil and gas based on a temperature rise rate and a pre-established relationship between the temperature rise rate and the lower limit temperature required for completely converting the convertible organic matter in the shale into the oil and the gas;
b) determining an optimal well distance of heating wells, based on a thermal field parameter of a target reservoir of interest, an optimal heating time corresponding to the lower limit temperature, and a pre-established relationship between the optimal well distance of the heating wells and the optimal heating time;
c) determining an oil yield equivalent of a production well in the target reservoir of interest, based on the temperature rise rate and a pre-established relationship between a temperature and an oil yield equivalent of the shale;
d) determining an effective heating region of a peripheral heating well based on the lower limit temperature; and
e) determining an optimal well pattern based on a boundary of the effective heating region of the peripheral heating well;
wherein the relationship between the temperature rise rate and the lower limit temperature required for completely converting the convertible organic matter in the shale into the oil and the gas, the relationship between the well distance of the heating wells and the optimal heating time, and the relationship between the temperature and the oil yield equivalent of the shale, and a plurality of thermal field varying with the temperature are pre-established and obtained by collecting a plurality of shale samples in the target reservoir of interest and performing a plurality of thermal simulation experiments on the plurality of shale samples according to an in-situ conversion exploitation condition;
wherein the plurality of thermal field parameters comprise a thermal diffusion coefficient, a specific heat capacity, and a thermal conductivity;
wherein the plurality of thermal simulation experiments, the thermal diffusion coefficient, the specific heat capacity e thermal conductivity are measured by using a laser thermal conductivity instrument, a simultaneous thermal analyzer and a thermal dilatometer respectively;
wherein the lower limit temperature, the optimal well distance of the heating wells, the oil yield equivalent and the optimal well pattern are optimal parameters in the optimal exploitation approach for the shale oil in-situ conversion; and
wherein the completely converting of convertible organic matter in the shale into the oil and the gas refers to a converted volume ratio of the convertible organic matter being 100%.

14. The apparatus according to claim 13, wherein the determining the optimal well pattern based on the boundary of the effective heating region of the peripheral heating well comprises:
wherein when a vertical well pattern is adopted for the heating wells, boundaries of effective heating regions or outermost boundaries of the effective heating regions outside peripheral heating wells for adjacent development well groups overlap, and a distance between outer boundaries of the effective heating regions outside the peripheral heating wells of exploitation units is from 0.5 m to 5 m; and
wherein when a horizontal well pattern is adopted for the heating wells, in a lateral direction, the outer boundaries of the effective heating regions or the outermost boundaries of the effective heating regions outside respective peripheral heating wells for the adjacent development well groups overlap, and the distance between the outer boundaries of the effective heating regions outside the respective peripheral heating wells for adjacent exploitation units is from 0.5 m to 5 m.

15. The apparatus according to claim 13, wherein the relationship between the optimal well distance of the heating wells and the optimal heating time is pre-established according to the following process:
i) establishing a relationship between the thermal diffusion coefficient and a temperature based on thermal diffusion coefficients at different temperature points that are measured by the laser thermal conductivity instrument in the plurality of thermal simulation experiments;
ii) establishing a relationship between the specific heat capacity and the temperature based on specific heat capacities at the different temperature points that are measured by the simultaneous thermal analyzer in the plurality of thermal simulation experiments;
iii) establishing a relationship between a shale thermal conductivity and the temperature based on shale densities at the different temperature points that are measured by the thermal dilatometer in the plurality of thermal simulation experiments; and
iv) establishing a relationship between the optimal well distance of the heating wells and the optimal heating time, by determining, through thermal field simulation, various optimal heating times with which all effective heating regions of the shale reach the lower limit temperature under a condition of various well distances of the heating wells, based on the relationship between the thermal diffusion coefficients and the temperature, the relationship between the specific heat capacity and the temperature, and the relationship between the shale thermal conductivity and the temperature.

16. The apparatus according to claim 13, wherein the processor further implements, when executing the computer program, the acts of:
a) for determining the converted volume ratio of the convertible organic matter in a development well group of the target reservoir of interest, based on the well distance of the heating wells and a pre-established relationship between the well distance of the heating wells and the converted volume ratio of the convertible organic matter in the development well group;
wherein the converted volume ratio of the convertible organic matter in the development well group refers to a ratio of a volume of the convertible organic matter that totally becomes oil and gas within a plane projection area of the effective heating region to a volume of the effective shale within the plane projection area of the effective heating region, when a temperature at a center of a connection line between the heating wells reaches the lower limit temperature within one in-situ conversion exploitation well group; and
b) determining a recovery ratio of the recoverable oil equivalent within one development well group with the optimal well pattern when the temperature at the center of the connection line between the heating wells reaches the lower limit temperature, based on the well distance of the heating wells, a number of layers in the well pattern of the target reservoir of interest, and a pre-established relationship among the well distance of the heating wells, the number of layers in the well pattern, and the recovery ratio of the recoverable oil equivalent within the development well group;

wherein the relationship among the well distance of the heating wells, the number of layers in the well pattern, and the recovery ratio of the recoverable oil equivalent within the development well group is pre-established by performing a plurality of thermal simulation experiments on a plurality of different shale samples in accordance with the in-situ conversion exploitation condition.

17. A non-transitory computer-readable medium storing therein a computer program for executing a method for predicting an optimal exploitation approach for shale oil in-situ conversion; comprising:

a) collecting a plurality of shale samples in a target reservoir of interest, and performing a plurality of thermal simulation experiments on a plurality of shale samples according to an in-situ conversion exploitation condition to pre-establish a relationship between a temperature rise rate and a lower limit temperature required for completely converting convertible organic matter in shale into oil and gas, a relationship between a well distance of heating wells and a beating time, and a relationship between a temperature and an oil yield equivalent of the shale, and to obtain a plurality of thermal field parameters varying with the temperature;

wherein the plurality of thermal parameters comprise a thermal diffusion coefficient, a specific heat capacity, nd a thermal conductivity; and wherein in the plurality of thermal simulation experiments, the thermal diffusion coefficient, the specific heat capacity, and the thermal conductivity are measured by using a laser thermal conductivity instrument simultaneous thermal analyzer, and a thermal dilatometer respectively;

b) determining the lower limit temperature required for completely converting the convertible organic matter in the shale to be measured into the oil and the gas; based on the temperature rise rate and a pre-established relationship between the temperature rise rate and the lower limit temperature required for completely converting the convertible organic matter in the shale into the oil and the gas;

c) determining an optimal well distance of the heating wells, based on a thermal field parameter the plurality of thermal field parameters of the target reservoir of interest, an optimal heating time corresponding to the lower limit temperature, and a pre-established relationship between the optimal well distance of the heating wells and the optimal heating time;

d) determining an oil yield equivalent of a production well in the target reservoir of interest; based on the temperature rise rate and a pre-established relationship between the temperature and the oil yield equivalent of the shale;

e) determining an effective heating region of a peripheral heating well based on the lower limit temperature; and f) determining an optimal well pattern; based on a boundary of the effective heating region of the peripheral heating well, wherein the lower limit temperature, the optimal well distance of the heating wells, the oil yield equivalent, and the optimal well pattern are optimal parameters in the optimal exploitation approach for shale oil in-situ conversion; and wherein the completely converting of convertible organic matter in shale into oil and gas refers to a converted volume ratio of the convertible organic natter being 100%.

18. The non-transitory computer-readable medium according to claim 17, wherein the determining the optimal well pattern based on the boundary of the effective heating region of the peripheral heating well depends on if the well pattern is vertical or horizontal;

wherein when a vertical well pattern is adopted for the heating wells, boundaries of effective heating regions or outermost boundaries of the effective heating regions outside peripheral heating wells for adjacent development well groups overlap, and a distance between the outer boundaries of the effective heating regions outside the peripheral heating wells of exploitation units is from 0.5 m to 5 m; and wherein when a horizontal well pattern is adopted for the heating wells, in a lateral direction, the outer boundaries of the effective heating regions or the outermost boundaries of the effective heating regions outside the respective peripheral heating wells for the adjacent development well groups overlap, and a distance between the outer boundaries of the effective heating regions outside the respective peripheral heating wells for adjacent exploitation units is from 0.5 m to 5 m.

19. The non-transitory computer-readable medium according to claim 17, wherein the relationship between the optimal well distance of heating wells and the optimal heating time is pre-established according to the following process:

i) establishing a relationship between the thermal diffusion coefficient and the temperature based on thermal diffusion coefficients at different temperature points that are measured by the laser thermal conductivity instrument in the plurality of thermal simulation experiment;

ii) establishing a relationship between the specific heat capacity and the temperature based on specific heat capacities at different temperature points that are measured by the simultaneous thermal analyzer in the thermal simulation experiment;

iii) establishing a relationship between shale thermal conductivity and the temperature based on shale densities at different temperature points that are measured by the thermal dilatometer in the thermal simulation experiment; and iv) establishing a relationship between the optimal well distance of the heating wells and the optimal heating time, by determining, through thermal field simulation, various optimal heating times with which all the effective heating regions of the shale reach the lower limit temperature under a condition of various well distances of the heating wells, based on the relationship between the thermal diffusion coefficients and the temperature, the relationship between the specific heat capacity and the temperature, and the relationship between the shale thermal conductivity and the temperature.

20. The non-transitory computer-readable medium according to claim 17, wherein the computer program is further configured to execute the acts of:
a) determining a converted volume ratio of the convertible organic matter in a development well group of the target reservoir of interest, based on the well distance of the heating wells and a pre-established relationship between the well distance of the heating wells and the converted volume ratio of the convertible organic matter in the development well group;
wherein the converted volume ratio of the convertible organic matter in the development well group refers to a ratio of a volume of the convertible organic matter that totally becomes oil and gas within a plane projection area of the effective heating region to a volume of the effective shale within the plane projection area of the effective heating region, when a temperature at a center of a connection line between the heating wells reaches the lower limit temperature within one in-situ conversion exploitation well group; and
b) determining a recovery ratio of the recoverable oil equivalent within one development well group with the optimal well pattern when the temperature at the center of the connection line between the heating wells reaches the lower limit temperature; based on the well distance of the heating wells, the number of layers in the well pattern of the target reservoir of interest, and a pre-established relationship among the well distance of the heating wells, the number of layers in the well pattern, and a recovery ratio of the recoverable oil equivalent within the development well group;
wherein the relationship among the well distance of the heating wells, the number of layers in the well pattern, and the recovery ratio of the recoverable oil equivalent within the development well group is pre-established by performing the plurality of thermal simulation experiments on a plurality of different shale samples in accordance with the in-situ conversion exploitation condition.

* * * * *